(12) United States Patent
Kidd et al.

(10) Patent No.: US 11,918,315 B2
(45) Date of Patent: Mar. 5, 2024

(54) DETERMINATION OF STRUCTURE AND TRAVERSAL OF OCCLUSIONS USING MAGNETIC PARTICLES

(71) Applicant: Pulse Therapeutics, Inc., St. Louis, MO (US)

(72) Inventors: Brian L. Kidd, Wildwood, MO (US); Sean C. Morris, Wildwood, MO (US); Michael E. Sabo, Prairie du Rocher, IL (US)

(73) Assignee: Pulse Therapeutics, Inc., St. Louis, MO (US)

( * ) Notice: Subject to any disclaimer, the term of this patent is extended or adjusted under 35 U.S.C. 154(b) by 1214 days.

(21) Appl. No.: 16/401,786

(22) Filed: May 2, 2019

(65) Prior Publication Data

US 2019/0336231 A1    Nov. 7, 2019

Related U.S. Application Data

(60) Provisional application No. 62/666,639, filed on May 3, 2018.

(51) Int. Cl.
   *A61B 34/00*       (2016.01)
   *A61K 41/00*       (2020.01)
   (Continued)

(52) U.S. Cl.
   CPC .............. *A61B 34/73* (2016.02); *A61K 41/00* (2013.01); *A61K 49/06* (2013.01);
   (Continued)

(58) Field of Classification Search
   CPC .... A61B 2017/00876; A61B 2090/374; A61B 2090/3762; A61B 2090/378; A61B 2090/3954; A61B 34/73; A61B 5/02007; A61B 5/0275; A61B 5/0515; A61B 5/055; A61B 6/504; A61B 8/0833; A61B 8/48;
   (Continued)

(56) References Cited

U.S. PATENT DOCUMENTS

| 3,474,777 A | 10/1969 | Figge et al. |
| 4,141,687 A | 2/1979 | Forrest et al. |

(Continued)

FOREIGN PATENT DOCUMENTS

| AU | 2010313105 | 6/2012 |
| CA | 2777841 | 5/2011 |

(Continued)

OTHER PUBLICATIONS

Yathindranath, V., et al. Simultaneous magnetically directed drug convection and MR imaging, Nanotechnology 20(40): paper #405101, 12 pgs. Sep. 2009-.

(Continued)

*Primary Examiner* — Yi-Shan Yang
*Assistant Examiner* — Alexei Bykhovski

(57) ABSTRACT

This disclosure generally relates to systems and methods for facilitating determination of morphology (e.g., shape) and structure (e.g., size, rigidity) and/or penetrating channels (e.g., microchannels) of occlusions (e.g., clots, fluid obstructions, tumors, chronic total occlusions) involving magnetic particles (e.g., nanoparticles, microparticles) controlled by an external magnetic control system.

20 Claims, 14 Drawing Sheets

MAGNETIC FIELD DIRECTION

(51) Int. Cl.
*A61K 49/06* (2006.01)
*A61B 90/00* (2016.01)

(52) U.S. Cl.
CPC . *A61B 2090/374* (2016.02); *A61B 2090/3762* (2016.02); *A61B 2090/378* (2016.02)

(58) Field of Classification Search
CPC ....... A61K 41/00; A61K 49/06; A61M 37/00; G01R 33/5601
See application file for complete search history.

(56) References Cited

U.S. PATENT DOCUMENTS

| | | |
|---|---|---|
| 4,359,453 A | 11/1982 | Gordon |
| 4,916,070 A | 4/1990 | Matsueda et al. |
| 5,078,140 A | 1/1992 | Kwoh |
| 5,110,727 A | 5/1992 | Oberhardt |
| 5,401,253 A | 3/1995 | Reynolds |
| 5,543,158 A | 8/1996 | Gref et al. |
| 5,654,864 A | 8/1997 | Ritter et al. |
| 5,665,277 A | 9/1997 | Johnson et al. |
| 5,916,539 A | 6/1999 | Pilgrimm |
| 5,931,818 A | 8/1999 | Werp et al. |
| 6,014,580 A | 1/2000 | Blume et al. |
| 6,015,414 A | 1/2000 | Werp et al. |
| 6,128,174 A | 10/2000 | Ritter et al. |
| 6,148,823 A | 11/2000 | Hastings |
| 6,152,933 A | 11/2000 | Werp et al. |
| 6,157,853 A | 12/2000 | Blume et al. |
| 6,212,419 B1 | 4/2001 | Blume et al. |
| 6,231,496 B1 | 5/2001 | Wilk et al. |
| 6,241,671 B1 | 6/2001 | Ritter et al. |
| 6,292,678 B1 | 9/2001 | Hall et al. |
| 6,296,604 B1 | 10/2001 | Garibaldi et al. |
| 6,304,768 B1 | 10/2001 | Blume et al. |
| 6,311,082 B1 | 10/2001 | Creighton, IV et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,358,244 B1 | 3/2002 | Newman et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,475,223 B1 | 11/2002 | Werp et al. |
| 6,482,436 B1 | 11/2002 | Volkonsky et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,529,761 B2 | 3/2003 | Creighton, IV et al. |
| 6,537,196 B1 | 3/2003 | Creighton, IV et al. |
| 6,541,039 B1 | 4/2003 | Lesniak et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,638,494 B1 | 10/2003 | Pilgrimm |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,740,103 B2 | 5/2004 | Hall et al. |
| 6,755,816 B2 | 6/2004 | Ritter et al. |
| 6,786,219 B2 | 9/2004 | Garibaldi et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,979,466 B2 | 12/2005 | Lesniak et al. |
| 6,980,843 B2 | 12/2005 | Eng et al. |
| 7,008,418 B2 | 3/2006 | Hall et al. |
| 7,010,338 B2 | 3/2006 | Ritter et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| 7,052,777 B2 | 3/2006 | Brotzman, Jr. et al. |
| 7,066,924 B1 | 6/2006 | Garibaldi et al. |
| 7,074,175 B2 | 7/2006 | Handy et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al. |
| 7,248,914 B2 | 7/2007 | Hastings et al. |
| 7,249,604 B1 | 7/2007 | Mohanraj |
| 7,264,584 B2 | 9/2007 | Ritter et al. |
| 7,276,044 B2 | 10/2007 | Ferry et al. |
| 7,286,034 B2 | 10/2007 | Creighton |
| 7,305,263 B2 | 12/2007 | Creighton, IV |
| 7,313,429 B2 | 12/2007 | Creighton, IV et al. |
| 7,329,638 B2 | 2/2008 | Yang et al. |
| 7,341,063 B2 | 3/2008 | Garbibaldi et al. |
| 7,346,379 B2 | 3/2008 | Eng et al. |
| 7,389,778 B2 | 6/2008 | Sabo et al. |
| 7,416,335 B2 | 8/2008 | Munger |
| 7,452,551 B1 | 11/2008 | Unger et al. |
| 7,459,145 B2 | 12/2008 | Bao et al. |
| 7,495,537 B2 | 2/2009 | Tunay |
| 7,502,640 B2 | 3/2009 | Conolly et al. |
| 7,505,615 B2 | 3/2009 | Viswanathan |
| 7,516,416 B2 | 4/2009 | Viswanathan et al. |
| 7,524,630 B2 | 4/2009 | Tan et al. |
| 7,537,570 B2 | 5/2009 | Kastelein |
| 7,540,288 B2 | 6/2009 | Viswanathan et al. |
| 7,540,866 B2 | 6/2009 | Viswanathan et al. |
| 7,543,239 B2 | 6/2009 | Viswanathan et al. |
| 7,555,331 B2 | 6/2009 | Viswanathan |
| 7,567,233 B2 | 7/2009 | Garibaldi et al. |
| 7,603,905 B2 | 10/2009 | Creighton, IV |
| 7,623,736 B2 | 11/2009 | Viswanathan |
| 7,625,382 B2 | 12/2009 | Werp et al. |
| 7,627,361 B2 | 12/2009 | Viswanathan |
| 7,630,752 B2 | 12/2009 | Viswanathan |
| 7,635,342 B2 | 12/2009 | Ferry et al. |
| 7,657,075 B2 | 2/2010 | Viswanathan |
| 7,662,126 B2 | 2/2010 | Creighton, IV |
| 7,690,619 B2 | 4/2010 | Wolfersberger |
| 7,708,696 B2 | 5/2010 | Ritter et al. |
| 7,713,239 B2 | 5/2010 | Uber, III et al. |
| 7,742,803 B2 | 6/2010 | Viswanathan et al. |
| 7,747,960 B2 | 6/2010 | Garibaldi et al. |
| 7,751,867 B2 | 7/2010 | Viswanathan |
| 7,756,308 B2 | 7/2010 | Viswanathan |
| 7,757,694 B2 | 7/2010 | Ritter et al. |
| 7,761,133 B2 | 7/2010 | Viswanathan et al. |
| 7,766,856 B2 | 8/2010 | Ferry et al. |
| 7,769,428 B2 | 8/2010 | Viswanathan et al. |
| 7,769,444 B2 | 8/2010 | Pappone |
| 7,771,415 B2 | 8/2010 | Ritter et al. |
| 7,771,437 B2 | 8/2010 | Hogg et al. |
| 7,772,950 B2 | 8/2010 | Tunay |
| 7,774,046 B2 | 8/2010 | Werp et al. |
| 7,815,580 B2 | 10/2010 | Viswanathan |
| 7,818,076 B2 | 10/2010 | Viswanathan |
| 7,831,294 B2 | 11/2010 | Viswanathan |
| 7,846,201 B2 | 12/2010 | Chorny et al. |
| 7,853,306 B2 | 12/2010 | Viswanathan et al. |
| 7,892,233 B2 | 2/2011 | Hall et al. |
| 7,961,924 B2 | 6/2011 | Viswanathan |
| 7,961,926 B2 | 6/2011 | Viswanathan |
| 7,966,059 B2 | 6/2011 | Creighton, IV et al. |
| 7,968,117 B1 | 6/2011 | Morrisson et al. |
| 7,983,733 B2 | 7/2011 | Viswanathan |
| 7,998,020 B2 | 8/2011 | Kidd et al. |
| 8,024,024 B2 | 9/2011 | Viswanathan et al. |
| 8,060,184 B2 | 11/2011 | Hastings et al. |
| 8,088,129 B2 | 1/2012 | Werp et al. |
| 8,092,450 B2 | 1/2012 | Davies et al. |

(56) References Cited

U.S. PATENT DOCUMENTS

| | | |
|---|---|---|
| 8,114,032 B2 | 2/2012 | Ferry et al. |
| 8,135,185 B2 | 3/2012 | Blume et al. |
| 8,162,920 B2 | 4/2012 | Ritter et al. |
| 8,192,374 B2 | 6/2012 | Viswanathan |
| 8,196,590 B2 | 6/2012 | Sabo et al. |
| 8,246,975 B2 | 8/2012 | Eguchi et al. |
| 8,251,885 B2 | 8/2012 | Ueda et al. |
| 8,278,274 B2 | 10/2012 | Bussat et al. |
| 8,293,213 B2 | 10/2012 | Schwartz et al. |
| 8,308,628 B2 | 11/2012 | Creighton |
| 8,313,422 B2 | 11/2012 | Creighton |
| 8,369,934 B2 | 2/2013 | Viswanathan |
| 8,500,619 B2 | 8/2013 | Brown et al. |
| 8,529,428 B2 | 9/2013 | Creighton |
| 8,562,505 B2 | 10/2013 | Levy et al. |
| 8,568,286 B2 | 10/2013 | Sih et al. |
| 8,579,787 B2 | 11/2013 | Shapiro et al. |
| 8,689,800 B2 | 4/2014 | Lin et al. |
| 8,691,261 B2 | 4/2014 | Eguchi et al. |
| 8,715,150 B2 | 5/2014 | Creighton |
| 8,888,674 B2 | 11/2014 | Shapiro et al. |
| 8,897,856 B2 | 11/2014 | Gaitas |
| 8,926,491 B2 | 1/2015 | Creighton |
| 8,968,699 B2 | 3/2015 | Jin et al. |
| 9,028,829 B2 | 5/2015 | Levy et al. |
| 9,108,035 B2 | 8/2015 | Shapiro et al. |
| 9,138,293 B1 | 9/2015 | Weisman |
| 9,339,664 B2 | 5/2016 | Creighton |
| 9,345,498 B2 | 5/2016 | Creighton |
| 9,883,878 B2 | 2/2018 | Creighton et al. |
| 10,029,008 B2 | 7/2018 | Creighton |
| 10,159,734 B2 | 12/2018 | Creighton |
| 10,646,241 B2 | 5/2020 | Creighton et al. |
| 10,813,997 B2 | 10/2020 | Creighton |
| 11,000,589 B2 | 5/2021 | Creighton |
| 11,406,711 B2 | 8/2022 | Creighton |
| 2001/0038683 A1 | 11/2001 | Ritter et al. |
| 2002/0019644 A1 | 2/2002 | Hastings et al. |
| 2002/0072662 A1 | 6/2002 | Hall et al. |
| 2002/0100486 A1 | 8/2002 | Creighton et al. |
| 2002/0103426 A1 | 8/2002 | Segner et al. |
| 2002/0103430 A1 | 8/2002 | Hastings et al. |
| 2002/0115904 A1 | 8/2002 | Ren |
| 2002/0159951 A1 | 10/2002 | Unger et al. |
| 2003/0009094 A1 | 1/2003 | Segner et al. |
| 2003/0028071 A1 | 2/2003 | Handy et al. |
| 2003/0086867 A1 | 5/2003 | Lanza et al. |
| 2003/0105382 A1 | 6/2003 | Brown et al. |
| 2003/0181809 A1 | 9/2003 | Hall et al. |
| 2003/0220667 A1 | 11/2003 | Van Der Burg |
| 2004/0002654 A1 | 1/2004 | Davidson et al. |
| 2004/0006301 A1 | 1/2004 | Sell et al. |
| 2004/0006350 A1 | 1/2004 | Hogg et al. |
| 2004/0064153 A1 | 4/2004 | Creighton et al. |
| 2004/0077942 A1 | 4/2004 | Hall et al. |
| 2004/0096511 A1 | 5/2004 | Harburn et al. |
| 2004/0133118 A1 | 7/2004 | Llinas |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0186376 A1 | 9/2004 | Hogg et al. |
| 2004/0196127 A1 | 10/2004 | Perrin |
| 2004/0253183 A1 | 12/2004 | Uber, III et al. |
| 2004/0254419 A1 | 12/2004 | Wang et al. |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0025797 A1 | 2/2005 | Wang et al. |
| 2005/0033162 A1 | 2/2005 | Garibaldi et al. |
| 2005/0065435 A1 | 3/2005 | Rauch et al. |
| 2005/0079132 A1 | 4/2005 | Wang et al. |
| 2005/0090732 A1 | 4/2005 | Ivkov et al. |
| 2005/0113628 A1 | 5/2005 | Creighton et al. |
| 2005/0113812 A1 | 5/2005 | Viswanathan et al. |
| 2005/0119556 A1 | 6/2005 | Gillies et al. |
| 2005/0119687 A1 | 6/2005 | Dacey et al. |
| 2005/0182315 A1 | 8/2005 | Ritter et al. |
| 2005/0256398 A1 | 11/2005 | Hastings et al. |
| 2005/0271732 A1 | 12/2005 | Seeney et al. |
| 2005/0271745 A1 | 12/2005 | Gruettner et al. |
| 2005/0273130 A1 | 12/2005 | Sell |
| 2005/0281858 A1 | 12/2005 | Kloke et al. |
| 2006/0025675 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036163 A1 | 2/2006 | Viswanathan |
| 2006/0041181 A1 | 2/2006 | Viswanathan et al. |
| 2006/0094956 A1 | 5/2006 | Viswanathan |
| 2006/0142630 A1 | 6/2006 | Meretei |
| 2006/0142632 A1 | 6/2006 | Meretei |
| 2006/0142749 A1 | 6/2006 | Ivkov |
| 2006/0144407 A1 | 7/2006 | Aliberto et al. |
| 2006/0144408 A1 | 7/2006 | Ferry |
| 2006/0165805 A1 | 7/2006 | Steinhoff et al. |
| 2006/0228421 A1 | 10/2006 | Seeney et al. |
| 2006/0270948 A1 | 11/2006 | Viswanathan et al. |
| 2006/0276867 A1 | 12/2006 | Viswanathan |
| 2006/0278248 A1 | 12/2006 | Viswanathan |
| 2006/0281990 A1 | 12/2006 | Viswanathan et al. |
| 2007/0010702 A1 | 1/2007 | Wang et al. |
| 2007/0016010 A1 | 1/2007 | Creighton et al. |
| 2007/0016131 A1 | 1/2007 | Munger et al. |
| 2007/0021731 A1 | 1/2007 | Garibaldi et al. |
| 2007/0021744 A1 | 1/2007 | Creighton |
| 2007/0032746 A1 | 2/2007 | Sell |
| 2007/0038065 A1 | 2/2007 | Creighton et al. |
| 2007/0038074 A1 | 2/2007 | Ritter et al. |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0062546 A1 | 3/2007 | Viswanathan et al. |
| 2007/0135804 A1 | 6/2007 | Ritter et al. |
| 2007/0148634 A1 | 6/2007 | Bruchez et al. |
| 2007/0149946 A1 | 6/2007 | Viswanathan et al. |
| 2007/0167720 A1 | 7/2007 | Viswanathan et al. |
| 2007/0191671 A1 | 8/2007 | Kawano et al. |
| 2007/0197899 A1 | 8/2007 | Ritter et al. |
| 2007/0197906 A1 | 8/2007 | Ritter |
| 2007/0225589 A1 | 9/2007 | Viswanathan |
| 2007/0231393 A1 | 10/2007 | Ritter et al. |
| 2007/0250041 A1 | 10/2007 | Werp |
| 2007/0270686 A1 | 11/2007 | Ritter et al. |
| 2007/0287909 A1 | 12/2007 | Garibaldi et al. |
| 2008/0004595 A1 | 1/2008 | Viswanathan et al. |
| 2008/0006280 A1 | 1/2008 | Aliberto et al. |
| 2008/0015427 A1 | 1/2008 | Kastelein et al. |
| 2008/0016677 A1 | 1/2008 | Creighton |
| 2008/0039705 A1 | 2/2008 | Viswanathan |
| 2008/0039830 A1 | 2/2008 | Munger et al. |
| 2008/0045865 A1 | 2/2008 | Kislev |
| 2008/0047568 A1 | 2/2008 | Ritter et al. |
| 2008/0058608 A1 | 3/2008 | Garibaldi et al. |
| 2008/0058609 A1 | 3/2008 | Garibaldi et al. |
| 2008/0059598 A1 | 3/2008 | Garibaldi et al. |
| 2008/0064933 A1 | 3/2008 | Garibaldi et al. |
| 2008/0065061 A1 | 3/2008 | Viswanathan |
| 2008/0092993 A1 | 4/2008 | Creighton |
| 2008/0097200 A1 | 4/2008 | Blume et al. |
| 2008/0114335 A1 | 5/2008 | Flickinger et al. |
| 2008/0200913 A1 | 8/2008 | Viswanathan |
| 2008/0208912 A1 | 8/2008 | Garibaldi |
| 2008/0228065 A1 | 9/2008 | Viswanathan et al. |
| 2008/0228068 A1 | 9/2008 | Viswanathan et al. |
| 2008/0287909 A1 | 11/2008 | Viswanathan et al. |
| 2008/0294232 A1 | 11/2008 | Viswanathan |
| 2008/0312673 A1 | 12/2008 | Viswanathan et al. |
| 2009/0012821 A1 | 1/2009 | Besson et al. |
| 2009/0062646 A1 | 3/2009 | Creighton, IV et al. |
| 2009/0062828 A1 | 3/2009 | Marr |
| 2009/0082722 A1 | 3/2009 | Munger et al. |
| 2009/0105579 A1 | 4/2009 | Garibaldi |

(56) References Cited

U.S. PATENT DOCUMENTS

| | | |
|---|---|---|
| 2009/0131798 A1 | 5/2009 | Minar et al. |
| 2009/0131927 A1 | 5/2009 | Kastelein et al. |
| 2009/0138009 A1 | 5/2009 | Viswanathan et al. |
| 2009/0148387 A1 | 6/2009 | Bikram |
| 2009/0177032 A1 | 7/2009 | Garibaldi et al. |
| 2009/0285759 A1 | 11/2009 | Ishikawa et al. |
| 2009/0287036 A1 | 11/2009 | Shapiro et al. |
| 2009/0297441 A1 | 12/2009 | Canham et al. |
| 2009/0299127 A1 | 12/2009 | Rudolph et al. |
| 2009/0306643 A1 | 12/2009 | Pappone et al. |
| 2010/0003197 A1 | 1/2010 | Bikram |
| 2010/0055042 A1 | 3/2010 | Yathindranath et al. |
| 2010/0063385 A1 | 3/2010 | Garibaldi et al. |
| 2010/0069733 A1 | 3/2010 | Kastelein et al. |
| 2010/0097315 A1 | 4/2010 | Garibaldi et al. |
| 2010/0137706 A1 | 6/2010 | Viswanathan |
| 2010/0163061 A1 | 7/2010 | Creighton |
| 2010/0168553 A1 | 7/2010 | Martel |
| 2010/0204674 A1 | 8/2010 | Forbes et al. |
| 2010/0222669 A1 | 9/2010 | Flickinger et al. |
| 2010/0233147 A1 | 9/2010 | Schwartz et al. |
| 2010/0269838 A1 | 10/2010 | Flanagan et al. |
| 2010/0298845 A1 | 11/2010 | Kidd et al. |
| 2011/0021970 A1 | 1/2011 | Vo-Dinh et al. |
| 2011/0022029 A1 | 1/2011 | Viswanathan |
| 2011/0028989 A1 | 2/2011 | Ritter et al. |
| 2011/0046618 A1 | 2/2011 | Minar et al. |
| 2011/0071335 A1 | 3/2011 | Ueda et al. |
| 2011/0087237 A1 | 4/2011 | Viswanathan |
| 2011/0111982 A1 | 5/2011 | Woodside et al. |
| 2011/0130718 A1 | 6/2011 | Kidd et al. |
| 2011/0152712 A1 | 6/2011 | Cao et al. |
| 2011/0215888 A1 | 9/2011 | Abbott et al. |
| 2011/0245581 A1 | 10/2011 | Schwartz et al. |
| 2011/0311457 A1 | 12/2011 | Skerrett et al. |
| 2012/0021010 A1 | 1/2012 | Deb et al. |
| 2012/0157824 A1 | 6/2012 | Bossmann et al. |
| 2012/0183475 A1* | 7/2012 | Michel ............... C08B 37/0063 435/7.1 |
| 2012/0226093 A1 | 9/2012 | Creighton |
| 2012/0232329 A1 | 9/2012 | Creighton |
| 2012/0296149 A1 | 11/2012 | Creighton |
| 2012/0310034 A1 | 12/2012 | Creighton |
| 2013/0023714 A1 | 1/2013 | Johnston et al. |
| 2013/0296631 A1 | 11/2013 | Weinberg et al. |
| 2014/0056813 A1* | 2/2014 | Pottier ............... A61K 41/0028 424/9.1 |
| 2014/0135564 A1 | 5/2014 | Creighton |
| 2014/0163367 A1 | 6/2014 | Eskuri |
| 2014/0248632 A1 | 9/2014 | Kopelman et al. |
| 2015/0099919 A1 | 4/2015 | Creighton |
| 2015/0230810 A1 | 8/2015 | Creighton et al. |
| 2015/0231282 A1 | 8/2015 | Pozzo et al. |
| 2015/0366574 A1 | 12/2015 | Kovarik et al. |
| 2015/0374395 A1* | 12/2015 | Creighton ............... A61P 9/14 604/500 |
| 2016/0066989 A1* | 3/2016 | Davies ............... A61B 18/1492 606/41 |
| 2017/0095675 A1 | 4/2017 | Creighton |
| 2017/0128571 A1 | 4/2017 | Creighton |
| 2017/0165020 A1 | 6/2017 | Martel |
| 2018/0221041 A1 | 8/2018 | Creighton et al. |
| 2019/0336231 A1 | 11/2019 | Kidd et al. |
| 2020/0085730 A1 | 3/2020 | Khizroev et al. |
| 2020/0330727 A1 | 10/2020 | Creighton |
| 2020/0330730 A1 | 10/2020 | Creighton |
| 2020/0360711 A1 | 11/2020 | Kidd et al. |
| 2021/0093339 A1 | 4/2021 | Creighton et al. |

FOREIGN PATENT DOCUMENTS

| | | |
|---|---|---|
| CA | 2934401 | 5/2011 |
| DE | 2450098 A1 | 4/1976 |
| DE | 102005030986 | 1/2007 |
| EP | 1001811 B1 | 9/2002 |
| IL | 219515 | 7/2016 |
| IL | 246714 | 11/2017 |
| JP | H07(1995)-500278 A | 1/1995 |
| JP | H07-213622 A | 8/1995 |
| JP | 2011-501751 A | 1/2011 |
| WO | WO 89/10788 | 11/1989 |
| WO | WO 2003/022360 | 3/2003 |
| WO | WO 2004/083902 A2 | 9/2004 |
| WO | WO 2005/011810 | 2/2005 |
| WO | WO 2005/072169 | 8/2005 |
| WO | WO 2006/035550 | 4/2006 |
| WO | WO 2007/125699 | 11/2007 |
| WO | WO 2008/95450 A | 8/2008 |
| WO | WO 2010/092495 | 8/2010 |
| WO | WO 2011/047313 | 4/2011 |
| WO | WO 2011/050085 | 4/2011 |
| WO | WO 2011/053984 | 5/2011 |
| WO | WO 2012/009675 | 1/2012 |
| WO | WO 2012/018290 | 2/2012 |
| WO | WO 2013/185032 | 12/2013 |
| WO | WO 2016/069982 | 5/2016 |
| WO | PCT/US2018/062610 | 11/2018 |
| ZA | 2012/02947 | 9/2013 |

OTHER PUBLICATIONS

Rosengart, AJ., et al., Magnetically Guided Plasminogen Activator-Loaded Designer Spheres for Acute Stroke Lysis, Medical Hypotheses and Research, 2(3): p. 413-424, Jul. 2005).

Ci Acar Hy, et al., Superparamagnetic nanoparticles stabilized by polymerized PEGylated coatings, Journal of magnetism and magnetic materials, 293(1):p. 107, May 2005.

Torno, MD, et al., Improvement of in vitro thrombolysis employing magnetically-guided microspheres, Thrombosis Research, 121(6): p. 799-811, Jan. 2008.

Califf, Robert M. et al., "Hemorrhagic Complications Associated With The Use Of Intravenous Tissue Plasminogen Activator In Treatment Of Acute Myocardial Infarction," The American Journal of Medicine, Sep. 1988, pp. 353-359, vol. 85, Issue 3.

Chen, Haitao, et al., "Capture of Magnetic Carriers Within Large Arteries Using External Magnetic Fields," Journal of Drug Targeting, May 2008, 16:4,262-268.

Grady, M.S. et al., "Nonlinear Magnetic Stereotaxis: Three-Dimensional, In Vivo Remote Magnetic Manipulation of A Small Object In Canine Brain," Medical Physics, vol. 17, No. 3, May/Jun. 1990, pp. 405-415.

Gupta, Ajay K. et al., "Synthesis And Surface Engineering of Iron Oxide Nanoparticles for Biomedical Applications," Biomaterials, vol. 26, Issue 18, Jun. 2005, pp. 3995-4021.

Leadley, Robert J. Jr., et al., "Contribution of In Vivo Models of Thrombosis to the Discovery and Development of Novel Antithrombotic Agents," Journal of Pharmacological and Toxicological Methods, Mar.-Apr. 2000, pp. 101-116, vol. 43, Issue 2.

Peasley, K.W., "Destruction of Human Immunodeficiency-Infected Cells by Ferrofluid Particles Manipulated by an External Magnetic Field: Mechanical Disruption and Selective Introduction of Cytotoxic or Antiretroviral Substances into Target Cells," Medical Hypothesis, Jan. 1996, pp. 5-12, vol. 46, Issue 1.

Pouliquen, D. et al., "Iron Oxide Nanoparticles for Use as an MRI Contrast Agent: Pharmacokinetics and Metabolism," Magnetic Resonance Imaging, 1991, pp. 275-283, vol. 9, Issue 3.

Sugimoto, Tadao, Egoa Matijevic, "Formation of Uniform Spherical Magnetite Particles by Crystallization from Ferrous Hydroxide Gels," Journal of Colloid and Interface Science, Mar. 1980, pp. 227-243, vol. 74, Issue 1.

Wu, Sau-Ching, et al., "Functional Production and Characterization of a Fibrin-Specific SingleChain Antibody Fragment from Bacillus Subtilis: Effects of Molecular Chaperones and a Wall-Bound Protease on Antibody Fragment Production," Applied and Environmental Microbiology, Jul. 2002, p. 3261-3269, American Society for Microbiology, 2002.

Yodh, Shyam B. et al., "A New Magnet System for Intravascular Navigation", Med. & Biol. Engng., vol. 6, pp. 143-147 (1968).

(56) References Cited

OTHER PUBLICATIONS

Cheng, Rui et al., "Acceleration of Tissue Plasminogen Activator Mediated Thrombolysis by Magnetically Powered Nanomotors," ACS Nano, Jul. 9, 2014, downloaded from https://pubs.acs.org on Jul. 13, 2014.
Houston Methodist. "Magnetic nanoparticles could stop blood clot-caused strokes." Newswise, Inc. Feb. 23, 2015. < http://www.newswise.com/articles/magnetic-nanoparticles-could-stop-blood-clot-caused-strokes>.
Chen, Jyh-Ping et al., Targeted delivery of tissue plasminogen activator by binding to silica-coated magnetic nanoparticle, International Journal of Nanomedicine, Sep. 26, 2012, pp. 5137-5149.
Yang et al., Bioconjugation of recombinant tissue plasminogen activator to magnetic nanocarriers for targeted thrombolysis, International Journal of Nanomedicine, Sep. 28, 2012, pp. 5159-5173.
Sun et al., Magnetic nanoparticle in MR Imagining and drug delivery; Advanced Drug Delivery Reviews, 60(11): p. 1252-1265, Aug. 2008.
Drozdov, Andrey et al., Leach-proof magnetic thrombolytic nanoparticles and coatings of enhanced activity, published Jun. 20, 2016; Scientific Reports; pp. 1-8.
El-Sherbiny, Ibrahim et al., Tissue plasminogen activiator-based clot busting: Controlled delivery approaches, Global Cardiology Science & Practice, Sep. 2014; pp. 337-349.
Friedrich, Ralf et al., Tissue Plasminogen Activator Binding to Superparamagnetic Iron Oxide Nanoparticle, Nanoscale Research Letters; 2016, pp. 1-11.
Hsu, Hao-Lung et al., Preparation of thermosensitive magnetic liposome encapsulated recombinant tissue plasminogen activator for targeted thrombolysis, Journal of Magnetism and Magnetic Materials, Oct. 2017, pp. 188-194.
Hu, Jiangnan et al., Magnetically active Fe3O4 nanorods loaded with tissue plasminogent activator for enhanced thrombolysis, Nano Research, 2016, pp. 2562-2661.
Voros Eszter et al., TPA Immobilization on Iron Oxide Nanocutes and Localized Magnetic Hyperthermia Accelerate Blood Clot Lysis, Advanced Funtionsl Materials Journal, 2015, pp. 1709-1718.
Bartonkova H, Mashlan M. Medrik I, Jancik D, Zboril R. "Magnetically Modified Bentonite as a Possible Contrast Agent in MRI of Gatrointestinal Tract", 2007. Chem. Pap. 61 (5) 413-416. (Year: 2007).
U.S. Appl. No. 13/505,447 (U.S. Pat. No. 8,715,150), filed Aug. 21, 2012, Devices for Controlling Magnetic Nanoparticles to Treat Fluid Obstructions.
U.S. Appl. No. 13/471,871 (U.S. Pat. No. 8,308,628), filed May 15, 2012, Magnetic-Based Systems for Treating Occluded Vessels.
U.S. Appl. No. 13/471,908 (U.S. Pat. No. 8,313,422), filed May 15, 2012, Magnetic-Based Methods for Treating Vessel Obstructions.
U.S. Appl. No. 13/485,613 (U.S. Pat. No. 8,529,428), filed May 31, 2012, Methods of Controlling Magnetic Nanoparticles to Improve Vascular Flow.
U.S. Appl. No. 14/020,173 (U.S. Pat No. 8,926,491), filed Sep. 6, 2013, Methods of Controlling Magnetic Nanoparticles to Improve Vascular Flow.
U.S. Appl. No. 14/268,244 (U.S. Pat. No. 9,339,664), filed May 2, 2014, Control of Magnetic Rotors to Treat Therapeutic Targets.
U.S. Appl. No. 15/155,386 (U.S. Pat No. 10,029,008), filed May 16, 2016, Therapeutic Magnetic Control Systems.
U.S. Appl. No. 16/032,796, filed Jul. 11, 2018, Devices for Controlling Magnetic Nanoparticles to Treat Fluid Obstructions.
U.S. Appl. No. 14/400,999 (U.S. Pat. No. 9,883,878), filed Nov. 13, 2014, Magnetic-Based Systems and Methods for Manipulation of Magnetic Particles.
U.S. Appl. No. 15/886,130, filed Feb. 1, 2018, Detection of Fluidic Current Generated by Rotating Magnetic Particles.
U.S. Appl. No. 14/581,775 (U.S. Pat. No. 9,345,498), filed Dec. 23, 2014, Methods of Controlling Magnetic Nanoparticles to Improve Vascular Flow.
U.S. Appl. No. 15/160,944 (U.S. Pat. No. 10,159,734), filed May 20, 2016, Magnetic Particle Control.
U.S. Appl. No. 16/218,867, filed Dec. 13, 2018, Magnetic Particle Control and Visualization.
U.S. Appl. No. 16/401,786, filed May 2, 2019, Determination of Structure and Traversal of Occlusions Using Magnetic Particles.

\* cited by examiner

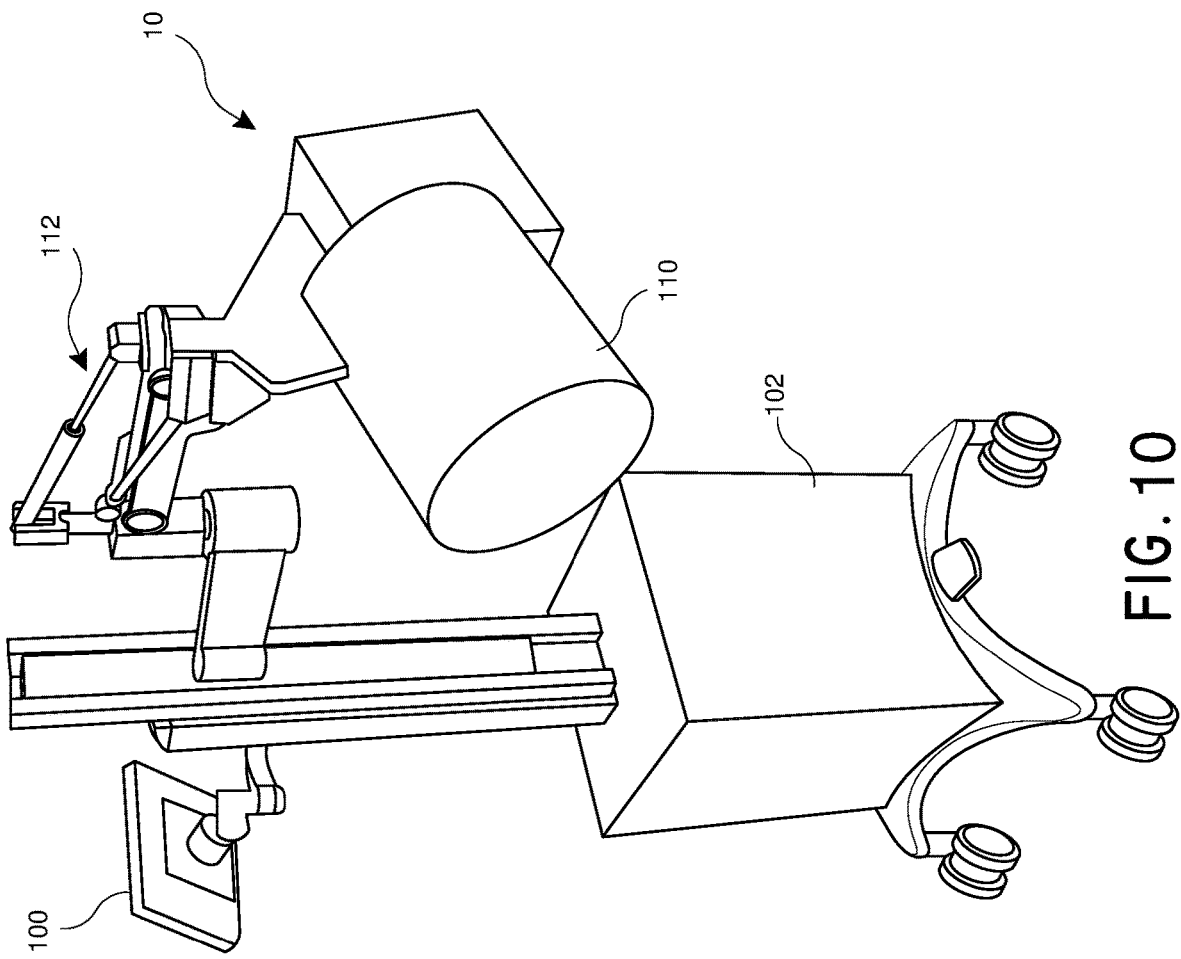

DETERMINATION OF STRUCTURE AND TRAVERSAL OF OCCLUSIONS USING MAGNETIC PARTICLES

RELATED APPLICATION

This application claims priority to U.S. Provisional Application No. 62/666,639 filed May 3, 2018, the entire content of which is hereby incorporated herein by reference.

FIELD

This disclosure generally relates to systems and methods for facilitating determination of morphology (e.g., shape) and structure (e.g., size, rigidity) and/or penetrating channels (e.g., microchannels) of occlusions (e.g., clots, fluid obstructions, tumors, chronic total occlusions) involving magnetic particles (e.g., nanoparticles, microparticles) controlled by an external magnetic control system and may also include an imaging modality or system.

SUMMARY

In accordance with several embodiments, a method of facilitating treatment of a therapeutic or diagnostic target (e.g., occlusion, obstruction, clot) within a body lumen, passage or organ (e.g., blood vessel) of a subject includes advancing a distal end of a microcatheter to a location proximal to, distal to or within the target and delivering magnetic particles (e.g., nanoparticles) through the microcatheter at the location of the target (e.g., clot). The occlusion or obstruction may comprise a clot, a thrombus, a chronic total occlusion, plaque buildup, a tumor or growth). The method also includes delivering a diagnostic agent through the microcatheter at the location of the target. The method further includes applying a rotating magnetic field so as to cause the magnetic particles (e.g., nanoparticles) to agglomerate into stir bars and to generate a circulating motion adjacent the target so as to cause at least some of the diagnostic agent to be driven into an outer surface of the target. The method also includes obtaining images indicative of a morphology (e.g., shape of an outer surface profile, presence of microchannels) of the target using an imaging modality capable of imaging the diagnostic agent and/or magnetic nanoparticles. In some methods, delivering the diagnostic agent is optional and imaging of just the magnetic particles that are driven into the outer surface of the target is performed (e.g., using an ultrasound-based imaging modality, a magnetic resonance imaging modality, and/or a tomography-based imaging modality).

Applying the rotating magnetic field may include rotating a permanent magnet positioned external to the subject. Rotating the permanent magnet may involve rotating the permanent magnet at a frequency of between 1 Hz and 10 Hz. A magnitude of the magnetic field may be between 0.01 and 1 Tesla. The method may further include delivering a therapeutic agent to the location of the clot (e.g., through the microcatheter). The diagnostic agent may comprise a contrast agent or a theranostic agent. In some embodiments, the diagnostic agent is attached to one or more of the magnetic nanoparticles.

In accordance with several embodiments, a method of facilitating treatment of a therapeutic target (e.g., target for treatment or diagnosis) within a body of a subject includes delivering magnetic particles (e.g., magnetic nanoparticles, magnetic microparticles) to a location near the therapeutic target within the body of the subject and applying a rotating magnetic field so as to cause the magnetic particles to agglomerate into stir bars and to generate a circulating motion (e.g., create micro-currents) adjacent the therapeutic target so as to cause the magnetic particles to be driven within channels or voids present within the therapeutic target or so as to cause the magnetic particles to be driven into an outer surface of the target (e.g., within and through one or more of the channels or voids, potentially even to a location downstream or beyond the target or occlusion to additional targets or occlusions). The method also includes obtaining images indicative utilizing an imaging modality (e.g., ultrasound-based imaging modality) capable of imaging the magnetic particles or alternatively obtaining images indicative of the channels or voids present within the therapeutic target determined from imaging of the magnetic particles utilizing the imaging modality.

At least some of the magnetic particles may comprise a diagnostic or theranostic agent, thereby being capable of being imaged using the imaging modality without separately introducing a diagnostic agent and/or cable of providing treatment to the therapeutic target without separately introducing a therapeutic agent. In some embodiments, the method includes delivering a therapeutic agent to the location of the therapeutic target. The therapeutic agent may be selected based, at least in part, on information derived from the obtained images.

The method may include delivering a diagnostic or theranostic agent to the location of the therapeutic target, wherein the circulating motion of the stir rods causes at least some of the diagnostic or theranostic agent to be driven within the channels or voids of the therapeutic target, and wherein the imaging modality is configured to obtain images based on the diagnostic or theranostic agent. In some implementations, the therapeutic target is an occlusion (e.g., chronic total occlusion) that is desired to be traversed or crossed by the diagnostic or theranostic agent (or a separate guidewire or access instrument). The circulating motion (e.g., micro-currents) generated by the stir rods can cause channels covered by flaps or hinges to be exposed and then traversed or crossed by the diagnostic or theranostic agent (or a separate guidewire or access instrument). The circulating motion (e.g., micro-currents) generated by the stir rods can also advantageously cause debris present within one or more channels (e.g., a largest central channel of a chronic total occlusion) to be removed, thereby facilitating penetration into and/or beyond an occlusion by a guidewire or access instrument or by a diagnostic agent (e.g., contrast agent) or theranostic agent. In some instances, additional therapeutic targets may be targeted downstream or beyond the initial therapeutic target (e.g., obstruction or occlusion).

The imaging modality utilized may include one or more of a magnetic resonance imaging modality, an ultrasound-based imaging modality, a tomography-based imaging modality (e.g., computed tomography or positron emission tomography), or any other imaging modality such as those described herein. The methods may also include adjusting the treatment of the therapeutic target at least in part based on information derived from the images. For example, a clinician may select a particular access or treatment instrument or a particular treatment approach based at least in part on information derived from the images (such as shape of an outer surface profile of the therapeutic target, or the location or presence of voids or channels within the therapeutic target). Delivering magnetic particles to the location near the therapeutic target within the body of the subject may include injecting the magnetic particles locally through a catheter or using transdermal needle-guided access performed using the imaging modality. The magnetic particles and the diagnostic or theranostic agent may be co-administered together at the same time or delivered separately. The methods described herein may be performed in an angiography suite or other operating room or clinical treatment site.

The methods summarized above and set forth in further detail below may describe certain actions taken by a practitioner; however, it should be understood that they can also include the instruction of those actions by another party. For example, actions such as "advancing a microcatheter" include "instructing the advancement of a microcatheter." Further aspects of embodiments of the inventions will be discussed in the following portions of the specification. With respect to the drawings, elements from one figure may be combined with elements from the other figures.

BRIEF DESCRIPTION OF THE DRAWINGS

The drawings, which are briefly described below, are for illustrative purposes only. The drawings are not intended to limit the scope of the disclosure in any way and may not be to scale.

FIG. 10 illustrates an example of a magnetic control system in accordance with various implementations.

DETAILED DESCRIPTION

Abbreviations and Definitions

Figure 1:
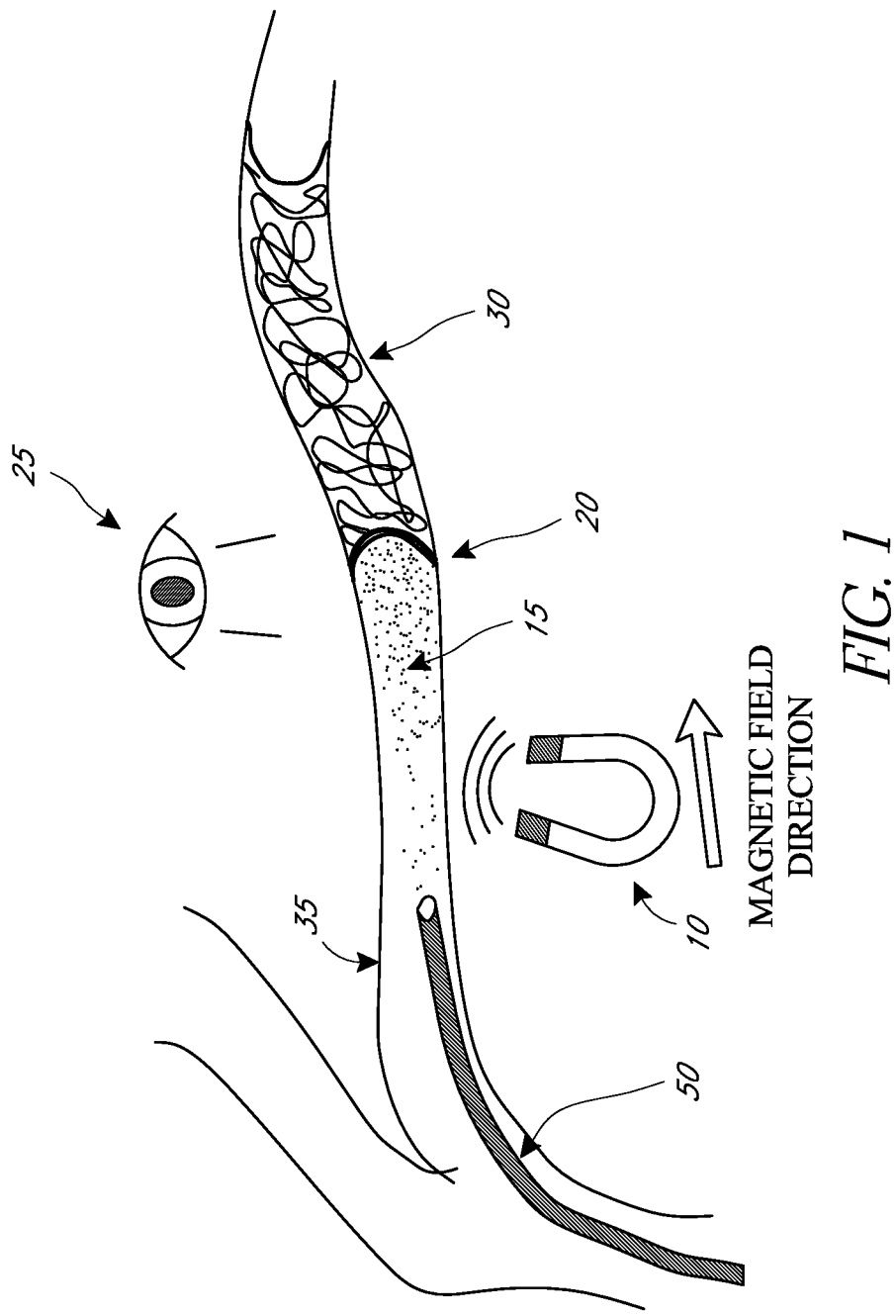
FIG. 1 illustrates a schematic embodiment of a system and method of using a magnetic control system in conjunction with magnetic particles, a diagnostic or theranostic agent, and an imaging modality, to determine morphology (e.g., a shape of a profile) of an obstruction within a vessel.

The scientific and technical terms used in connection with the disclosure shall have their ordinary meanings (e.g., as commonly understood by those of ordinary skill in the art) in addition to any definitions included herein. Further, unless otherwise required by context, singular terms shall include pluralities and plural terms shall include the singular.

"Patient" or "subject" shall be given its ordinary meaning and shall include, without limitation, human and veterinary subjects.

"Therapeutic agents" shall be given its ordinary meaning and shall include, without limitation, drugs or compositions capable of degrading a blood clot or atherosclerotic plaque (e.g., chronic total occlusion). For example, a thrombolytic drug can include tissue plasminogen activator (tPA), plasminogen, streptokinase, urokinase, recombinant tissue plasminogen activators (rtPA), alteplase, reteplase, tenecteplase, collagenase, and other drugs, and can include these drugs administered alone or co-administered with warfarin and/or heparin. Different thrombolytic drugs can be used in the thrombolytic process for different types of occlusions.

"Magnetic particle" shall be given its ordinary meaning and shall include, without limitation, magnetic nanoparticles having a diameter greater than or equal to about 1 nm and/or less than or equal to about 1000 nm, greater than or equal to about 10 nm and/or less than or equal to about 200 nm, greater than or equal to about 15 nm and/or less than or equal to about 150 nm, greater than or equal to about 20 nm and/or less than or equal to about 60 nm, 80 nm, 100 nm, and all integer values between 1 nm and 1000 nm, e.g., 1, 2, 3, 4, 5, . . . 997, 998, 999, and 1000. Magnetic particles may also include microparticles having a diameter greater than 1000 nm. The appropriate sizes of magnetic particles can depend on the therapeutic target of the system (e.g., very small vessels can accept smaller nanoparticles and larger parts of a circulatory system can accept larger nanoparticles). Examples of such magnetic nanoparticles include ferrimagnetic iron oxide nanoparticles. The particles may be made of magnetite or iron oxide and, in some embodiments, can be co-administered, coated or conjugated with one or more of the following: (1) diagnostic agents which allow visualization with an imaging modality (e.g., magnetic resonance imaging, X-ray, Positron Emission Tomography (PET), ultrasound, fluoroscopy, magnetic localization, computed tomography imaging (CT) or other imaging technologies; (2) therapeutic agents adapted to treat a therapeutic target (e.g., a circulatory system blockage, occlusion, obstruction, clot); and (3) theranostic agents adapted to provide both therapeutic and diagnostic capabilities.

"Fluid obstruction" shall be given its ordinary meaning and shall include, without limitation, a blockage, either partial or complete, that impedes the normal flow of fluid through the circulatory system (including the venous system and arterial system), the central nervous system, and the lymphatic system. "Vascular occlusions" are fluid obstructions that include, but are not limited to, atherosclerotic plaques, fatty buildup, fibrous caps, arterial stenosis, chronic total occlusion areas, restenosis, vein thrombi, cerebral thrombi, embolisms, hemorrhages, other blood clots, and very small vessels. Sometimes, fluid obstructions are generally referred to herein as "clots." The occlusions may completely or partially block flow through a vessel. Therapeutic targets, obstructions, and occlusions are considered to be used interchangeably in several embodiments described herein.

"Contrast Agent" and "Contrast Media" shall be given their ordinary meaning and shall include, without limitation, any material (solid or liquid) that facilitates visualization or imaging utilizing any imaging modality. Contrast media can be any substance used to enhance the contrast of structures or fluids within the body in medical imaging. The contrast media can include, for example, contrast agents, iodinated contrast media, ionic iodinated contrast media, lymphatic staining agents, magnetic resonance imaging contrast media, miscellaneous diagnostic dyes, non-iodinated contrast media, non-ionic iodinated contrast media, ultrasound contrast media, iodine, barium, gadolinium, ethiodoized oil, gadoterate meglumine, iodixanol, iohexol, microbubble contrast agents, radiopharmaceuticals, and/or any other contrast media. The contrast media may be delivered directly or locally to a target location through a catheter such as described herein, through systemic intravenous introduction, nasally, rectally, vaginally, orally, through inhalation to the lung, and by injection into muscle or skin or underneath the skin.

"Theranostic Agent" shall be given its ordinary meaning and shall include, without limitation, any material (solid or liquid) that provides combined therapeutic and diagnostic capabilities or effects. Theranostic agents may include any agents configured to simultaneously facilitate both therapy and diagnosis (e.g., radioiodine, biologics, iron oxide nanoparticles, quantum dots, carbon nanotubes, gold nanoparticles, and silica nanoparticles).

"Agglomerate" shall be given its ordinary meaning and shall include, without limitation, rotational clustering and chaining of a group of individual magnetic particles (e.g., nanoparticles, microparticles) in a manner to form "stir bars" or "stir rods" from the magnetic particles, as well as the combined structures themselves when used as a noun.

"Treatment" shall be given its ordinary meaning and shall include, without limitation, an approach for obtaining beneficial or desired clinical results. For purposes of this disclosure, beneficial or desired clinical results include, but are not limited to, one or more of the following: improvement or alleviation of any aspect of fluid obstruction within a body of a subject or within a device including, but not limited to, conditions caused by fluid obstructions (e.g., stroke, deep vein thrombosis, chronic total occlusion, myocardial infarction, pulmonary embolisms), coronary artery disease (e.g., chronic total occlusion), ischemic heart disease, atherosclerosis, and high blood pressure; cancer treatment; or movement along any body lumen, space, or cavity to access a desired treatment, or therapeutic, target.

Embodiments

Several embodiments of the inventions are particularly advantageous because they include one, several or all of the following benefits: (i) keeping diagnostic or therapeutic and/or theranostic agents at a target location longer than conventional approaches even when there is flow that would normally cause the agents to flow away; (ii) use of less contrast media than conventional techniques require, thereby reducing adverse effects due to exposure to large amounts of contrast media, such as kidney failure; (iii) more efficient travel of therapeutic or diagnostic and/or theranostic agents to target locations; (iv) more efficient or safer treatment through determination of morphology (e.g., profile shapes) of obstructions or presence of channels or voids through obstructions to inform subsequent treatment based on the determination; and/or (v) the ability of contrast agent/media or guidewires or other instruments to traverse through occlusions (e.g., chronic total occlusions) that could not be traversed otherwise.

Systems and methods for the physical manipulation of magnetic particles (e.g., nanoparticles) within body lumens (e.g., vasculature) of a subject to facilitate treatment of therapeutic targets (e.g., clearance of fluid obstructions) are described and illustrated in WIPO Publication No. WO 2011/053984 and WIPO Publ. No. WO 2013/173235, the entire contents of each of which are hereby incorporated by reference herein. The embodiments disclosed herein may be combined with and incorporated in conjunction with any of the embodiments or features of the magnetic control systems, therapeutic targets, or imaging or diagnostic methods disclosed in WIPO Publication No. WO 2013/173235, the entire contents of each of which are hereby incorporated by reference herein. For example, FIGS. 7A-7C and 8 included herein are from WIPO Publ. No. WO 2013/173235 to illustrate such example systems and methods.

In various aspects, the systems and methods described herein advantageously facilitate treatment of one or more therapeutic targets (e.g., clots, areas of chronic total occlusion, or tumors) by informing a clinician about the morphology (e.g., shape profile) and structure (e.g., whether the target is solid or has voids or microchannels) of the therapeutic target. The clinician may obtain this information using a system including a plurality of magnetic particles, a magnetic control system configured to controllably manipulate travel of the particles within a body of a patient from a location external to the patient, and a diagnostic and/or imaging system.

The system may further include a medical instrument (e.g., catheter, microcatheter, infusion catheter, infusion wire) configured to administer or deliver the magnetic particles within the patient. In some embodiments, magnetic particles (e.g., nanoparticles) are locally administered to a location near (e.g., proximate, adjacent) a therapeutic target or fluid obstruction through a catheter (e.g., a microcatheter). The medical instrument may be configured to inject the magnetic particles transcutaneously or transdermally through needle-guided access based on visualization using the diagnostic and/or imaging system. For example, computed tomography angiography or diagnostic ultrasound imaging systems and modalities can be used to identify a location of a therapeutic target (e.g., clot or area of occlusion, such as chronic total occlusion or a tumor). In some embodiments, a catheter is introduced intra-arterially and advanced to a location adjacent a clot within a cerebral artery, a coronary artery, any peripheral artery or any other artery.

In some embodiments, the magnetic particles themselves function as contrast agents that can be imaged or detected by an imaging modality without requiring delivery of a separate contrast media or agent to facilitate imaging. For example, the magnetic particles (e.g., monocrystalline or polycrystalline iron oxide nanoparticles) themselves may constitute contrast agents based on the makeup of the nanoparticles and can be opaque to certain imaging modalities or technologies. In various embodiments, the nanoparticles may comprise at least one of gadolinium, manganese, copper, nickel, cobalt, zinc, germanium, gold, silver, compounds comprising group II (A or B) and group VI elements, compounds comprising group IV and group VI elements, bioluminescence agents, combinations thereof, and the like. In some embodiments, the magnetic particles comprise theranostic structures, in that they provide both diagnostic and therapeutic capabilities. For example, the magnetic particles may include a therapeutic agent conjugated or coated or otherwise attached to the magnetic particles. Imaging of the magnetic particles can inform the clinician as to duration of time of exposure to the therapeutic agent, whether the therapeutic agent is administered separately or is a component of some or all of the magnetic particles.

In accordance with several embodiments, contrast media, bioluminescence or other materials may be attached to (e.g., conjugated to or adsorbed to) or doped into the magnetic particles (e.g., nanoparticles, microparticles) for chemical, magnetic, therapeutic, diagnostic, theranostic and/or imaging reasons. Example contrast coatings include contrast coatings detectable by X-ray, PET, MR and ultrasound imaging technologies.

In some embodiments, contrast media (e.g., diagnostic or theranostic agents) may be delivered together with the magnetic particles or separately from the magnetic particles to facilitate or enhance imaging (for example, if the magnetic particles themselves cannot be effectively imaged). The contrast media may be delivered through the same medical instrument and in the same manner as the magnetic particles or may be delivered separately (e.g., through systemic intravenous infusion or intra-arterial infusion through a separate catheter or other medical instrument). The contrast media and/or magnetic nanoparticles may be delivered to or through any body lumen, channel, space, volume or passage, including vasculature, Fallopian tubes, cerebrospinal spaces or passages, gastrointestinal tract (e.g., intestines, colon), ureters, lymphatic system (lymph nodes), intraosseous locations (e.g., bone cavities or spaces), liver, lungs, heart, pericardium, peritoneum, thoracic cavity, brain, etc. In some embodiments, the diagnostic agents (e.g., contrast media) are not attached to the particles but simply mixed with or co-administered with the particles.

The diagnostic or imaging modalities or technologies may include X-ray, ultrasound, radiography, magnetic resonance, nuclear medicine, photo acoustic, thermography, tomography (PET, CT), fluoroscopy, magnetic localization, and/or any other modalities or technologies. The imaging technologies and systems can be used to transmit images to a display device to provide an operator real-time feedback so that the operator can navigate or otherwise control movement of the magnetic particles (e.g., nanoparticles) and so that the operator can be informed regarding subsequent treatment of the therapeutic target.

The magnetic control systems and magnetic nanoparticles may be used in conjunction with any diagnostic or imaging scan, such as but not limited to angiograms, arteriograms, venograms, PET scans, CT scans, X-rays, elastography scans, lymphography scans, thermograms, sonograms, encephalograms, and/or the like. In certain implementations, control of the magnetic field by the magnetic control system may be integrated with control of the imaging modality (e.g., interlaced) by the imaging system to minimize interference between the systems and optimize performance (e.g., image display, magnetic field control, prevent aliasing due to overlapping or interfering frequency ranges).

As an example, a real-time user interface on a display can incorporate image information from a diagnostic or imaging system. The imaging system can be a system incorporating one or more imaging modalities, configured to provide imaging data to the magnetic control system. The imaging data can be derived from x-ray data, PET data, MR data, CT scan data, ultrasonic imaging data, or other imaging modality data, as described herein.

The operator may receive or view imaging data from the imaging system (e.g., on a display monitor communicatively coupled to the imaging system). In some embodiments, the imaging data comprises information derived from an imaging modality that, in use, provides information about the therapeutic target and/or about the magnetic particles, which can inform subsequent treatment of the therapeutic target by a clinician medical professional. For example, the imaging system can produce image data based on ultrasound-based imaging. The imaging system can transmit sound waves aimed at an area of interest and interpret the echoed waves to produce an image. The ultrasound-based imaging system can be configured to provide imaging data in real-time and can be configured to identify fluid flow, tissue, liquid, magnetic particles, and the like. In some embodiments, the information about the therapeutic target can include information about the morphology (e.g., shape) and structure (e.g., size, rigidity) and type of therapeutic target.

Identifying the magnetic particles can include analyzing the imaging data for signals associated with magnetic nanoparticles. For example, in ultrasonic imaging, the magnetic particles can have a distinctive signal in an image due to their motion, composition, position, behavior, orientation, or any combination of these. As another example, in PET systems, the magnetic particles can have a distinctive and/or identifiable signal in an image based on attached contrast agents, the density or composition of the particles, the position of the particles, or the like.

FIG. 1 illustrates a schematic embodiment of a system and method of using a magnetic control system 10 in conjunction with magnetic particles 15, a diagnostic or theranostic agent 20, and an imaging modality 25, to determine morphology (e.g., a shape of a profile) of an obstruction 30 (e.g., clot or area of occlusion, such as chronic total occlusion or tumor) within a vessel 35 or other body lumen or organ. The magnetic control system 10 can include any magnetic control system (such as those described herein or in WIPO Publ. No. 2013/173235) that facilitates control of orientation, position, rotation of a magnet or magnetic field. As shown in FIG. 1, the magnetic control system 10 includes a magnet (e.g., permanent magnet) that can be oriented, positioned and/or rotated (e.g., about multiple axes of rotation) to cause a magnetic field and gradient of the magnet to cause movement of magnetic particles 15 in a particular direction of travel. Electromagnets may also be used to accomplish magnetic control.

Figure 2:
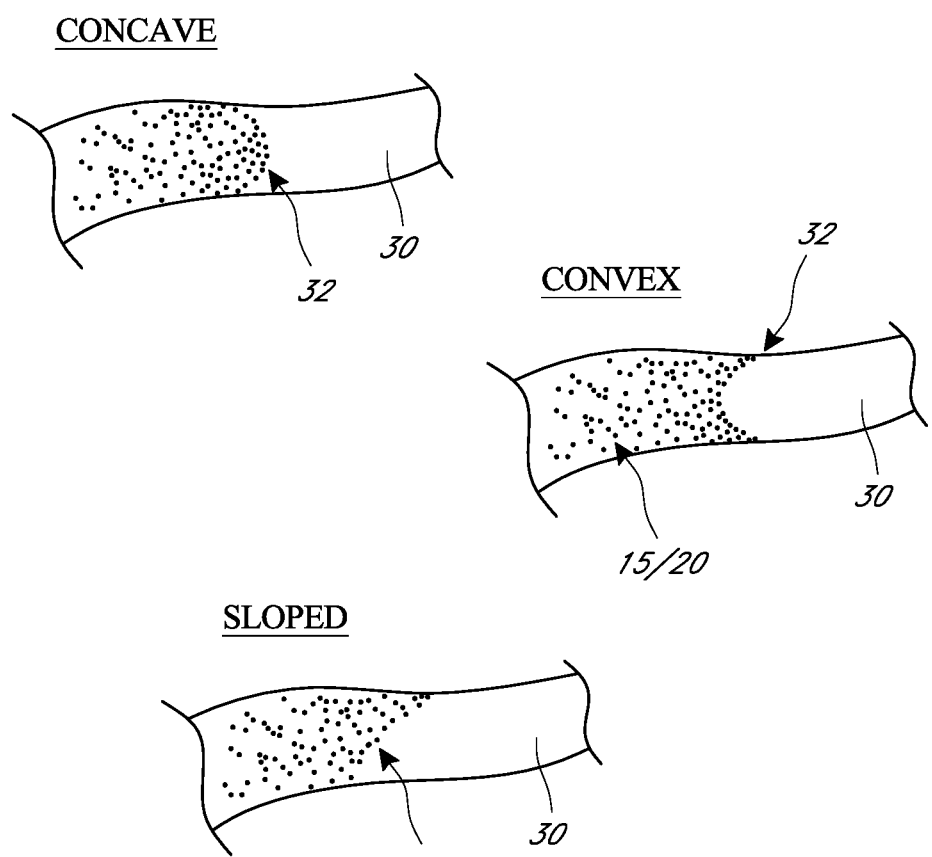
FIG. 2 illustrates various profile shapes of obstructions within a vessel that could be determined using the method and system schematically illustrated in FIG. 1.

If a diagnostic or theranostic agent 20 is provided separate from the magnetic particles 15, the movement of the magnetic particles 15 causes corresponding movement of the diagnostic or theranostic agent 20. In some cases, the interaction of the imaged particles or diagnostic agent with the surface of the therapeutic target 30 (e.g., clot, occlusion, chronic total occlusion, tumor) may be used to determine the morphology or profile shape (e.g., concave, convex, sloped) of the target (e.g., clot, tumor, fibrous cap). The magnetic particles 15 (and the diagnostic or theranostic agent if separate) may be driven into an outer surface (e.g., proximal surface, distal surface) of the therapeutic target 30 (e.g., clot) by the movement effected by the magnetic control system 10. The magnetic particles 15 (and the diagnostic or theranostic agent if separate) thus take the shape of the surface profile of the therapeutic target 30. The imaging system 25 is then used to obtain imaging data to display or otherwise convey the shape of the surface profile to the clinician or other medical professional. FIG. 2 illustrates various profile shapes (e.g., concave, convex, sloped) or face outlines 32 of obstructions 30 within a vessel 35 that could be determined using the methods and systems described herein.

The clinician or other medical professional may use the determined shape of the surface profile to inform a subsequent interventional approach. For example, if the therapeutic target 30 (e.g., clot or chronic total occlusion) is determined to have a concave cap or face outline 32, the clinician may proceed with more caution and may select a particular guidewire or other instrument to penetrate or traverse through the therapeutic target or occlusion that will reduce the likelihood of the instrument bouncing off the target surface or sliding toward a vessel or luminal wall and puncturing or perforating the wall (e.g., less rigid instrument or less sharp instrument). As another example, if the therapeutic target (e.g., clot or chronic total occlusion) or occlusion is determined to have a convex cap or face outline 32, the clinician may proceed with more flexibility in instrument selection (e.g., a more rigid instrument) and generally be more aggressive in the treatment because the access or treatment instrument is less likely to move toward a vessel or luminal wall and cause injury.

Figure 3:
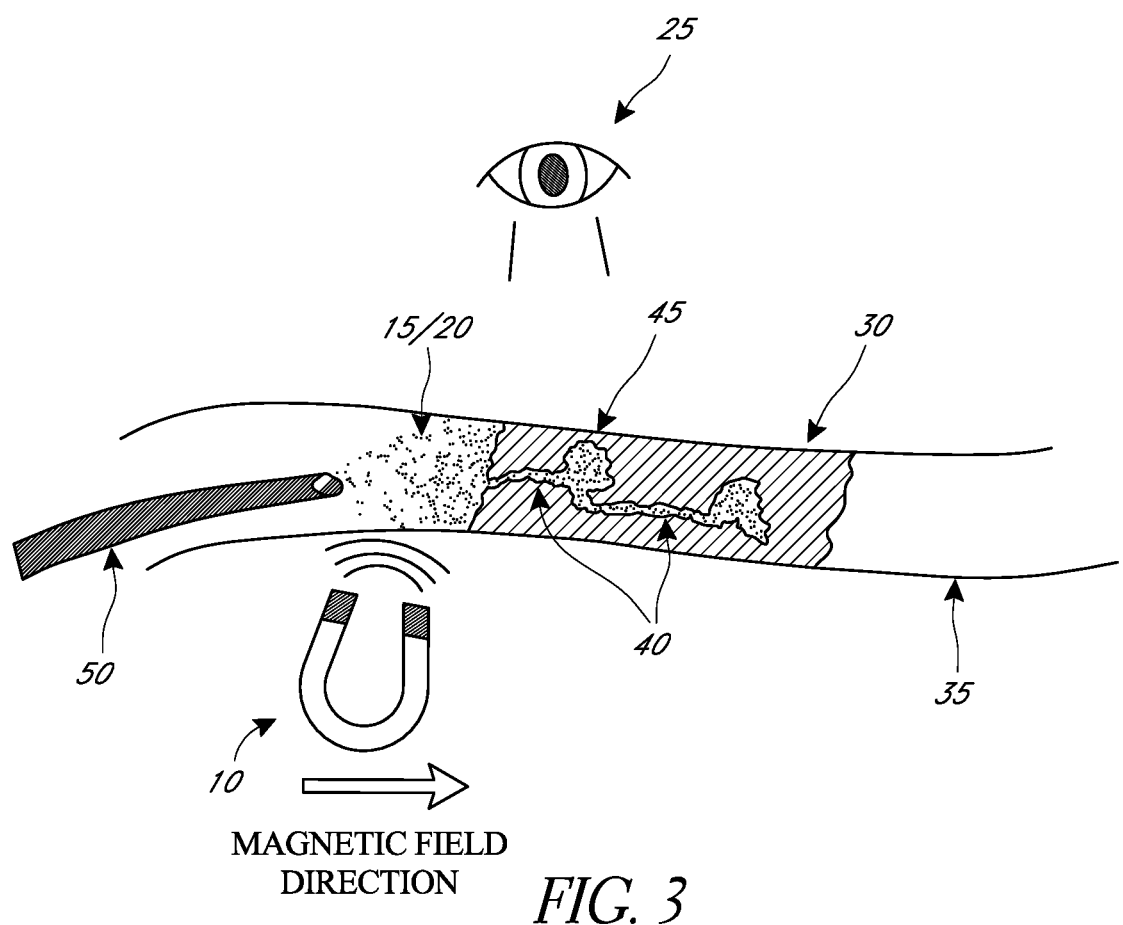
FIG. 3 illustrates a schematic embodiment of a system and method of using a magnetic control system in conjunction with magnetic particles, a diagnostic or theranostic agent, and an imaging modality, to identify and/or highlight microchannels or voids through or within an obstruction (e.g., clot or occlusion).

FIG. 3 illustrates a schematic embodiment of a system and method of using a magnetic control system 10 in conjunction with magnetic particles 15, a diagnostic or theranostic agent 20, and an imaging modality 25, to identify and/or highlight microchannels 40 and/or voids 45 extending completely or partially through or within an obstruction 30 (e.g., clot or occlusion or tumor). Penetration of magnetic particles 15 (e.g., magnetic nanoparticles, microparticles) and/or diagnostic or theranostic agent 20 into and/or through the therapeutic target 30 (e.g., clot, occlusion, tumor) may be used to identify underlying microchannels 40, voids 45, pockets, and/or caverns extending through or present within the therapeutic target 30. Such structural information may also be useful to inform subsequent treatment. For example, such information may allow a clinician to estimate length and age of the therapeutic target 30 or to estimate how solid or permeable the target 30 is likely to be and to tailor treatment accordingly based on the information.

As another example, the clinician may determine whether an occlusion 30 may be crossed or how the occlusion 30 can be most efficiently crossed (e.g., by identifying the less solid and more porous sections). In some embodiments, the clinician can traverse the occlusion or obstruction 30 by traversing a guidewire or other instrument through the microchannels 40 or voids 45 under direct visualization provided by the imaging system 25 that is imaging the contrast media 20 or magnetic particles 15 acting as contrast agents. In some embodiments, the microchannels 40 include a larger microchannel that extends through the entire length of the occlusion 30. As yet another example, the therapeutic agent to be used for treatment may be selected by the clinician based on the information (e.g., shape, structure, target type) obtained about the therapeutic target 30 from the imaging system 25.

Figure 4A:
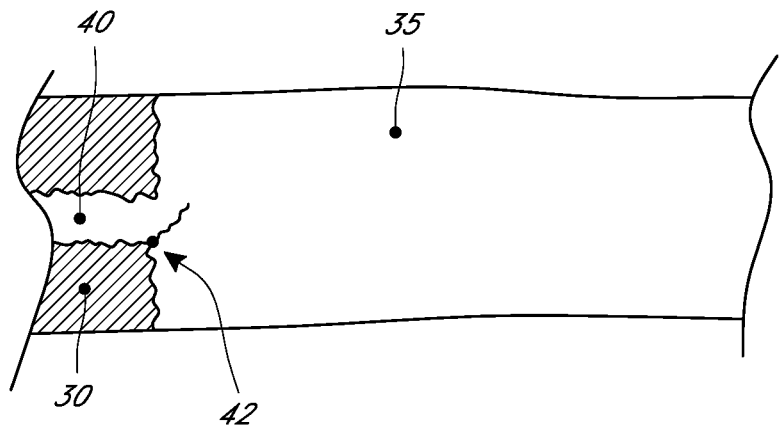
FIGS. 4A-4D schematically illustrate why traversal of occlusions is difficult or impossible without use of the inventive technology described in the present application.
Figure 4B:
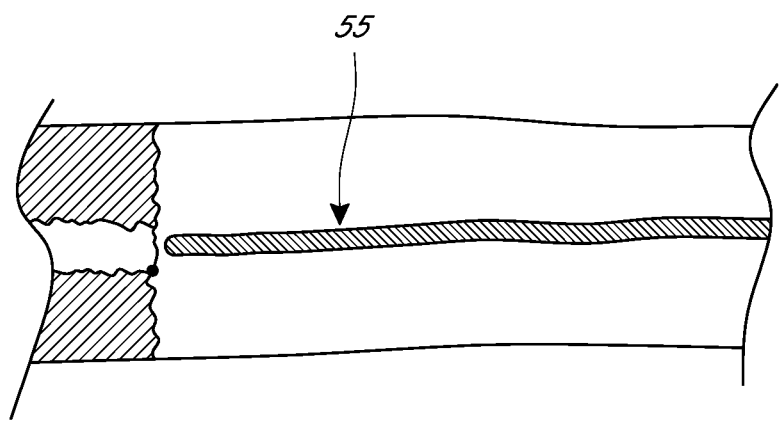
Figure 4C:
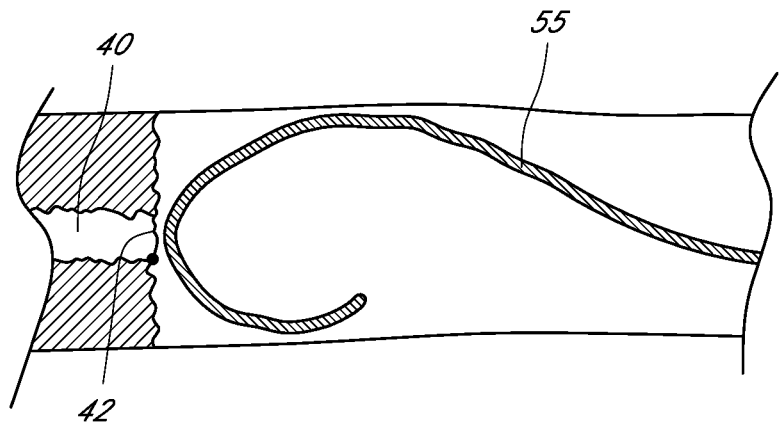
Figure 4D:
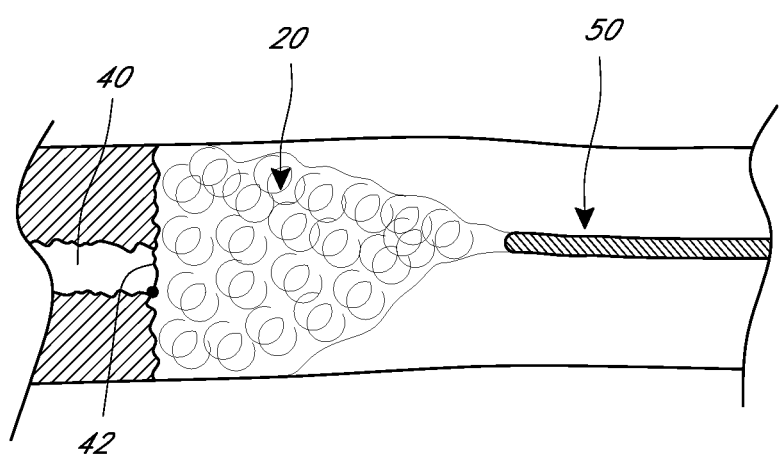

FIGS. 4A-4D schematically illustrate example reasons why traversal of occlusions 30 is difficult or impossible without use of the inventive technology described in the present application. As shown in FIG. 4A, the therapeutic target (e.g., occlusion) 30 can include a channel 40 covered by a hinged flap 42. In some instances, multiple hinged flaps may cover the channel 40. There may be multiple channels 40 each covered by one or more hinged flaps 42. Turning to FIG. 4B, if a guidewire or other instrument 55 is advanced along a vessel 35 in an attempt to traverse the occlusion 30 through the channel 40, the guidewire or other instrument 55 will most likely encounter the one or more hinged flaps 42 and effectively cause the hinged flap(s) 42 to seal off the channel 40 from entry. As shown in FIG. 4C, further advancement of the guidewire or other instrument 55 results in prolapse and/or buckling of the guidewire or other instrument 55, which may result in unwanted injury to the vessel 35. Turning to FIG. 4D, if contrast media 20 is injected toward the occlusion 30 from a catheter 50, the pressure from the contrast injection can act to close the hinged flap 42 as well, thereby causing the channel 40 to remain hidden and sealed off. Thus in most, if not all scenarios, it is difficult or impossible for a guidewire 55 or contrast media 20 to traverse the occlusion 30.

Figure 5A:
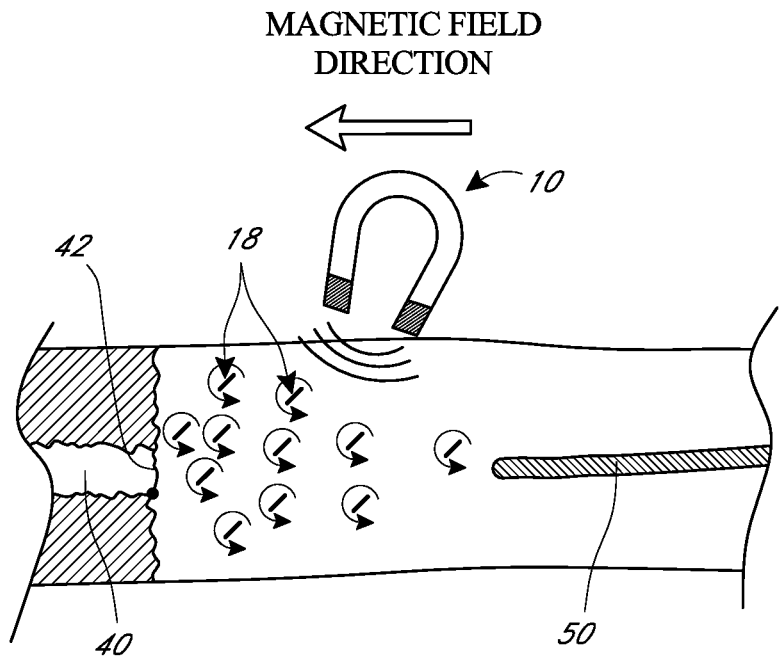
FIGS. 5A-5C schematically illustrate the mechanism of action of the inventive technology described herein that advantageously allows for traversal of occlusions.
Figure 5B:
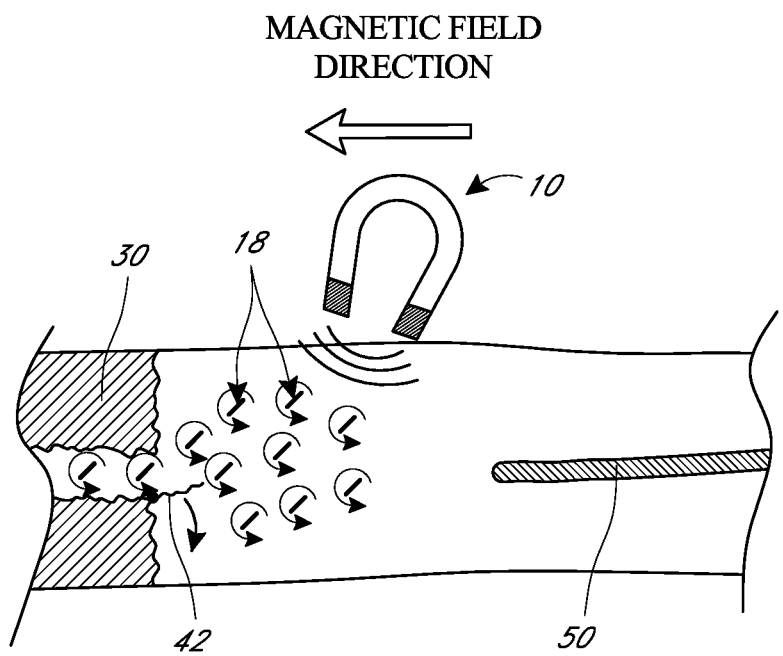
Figure 5C:
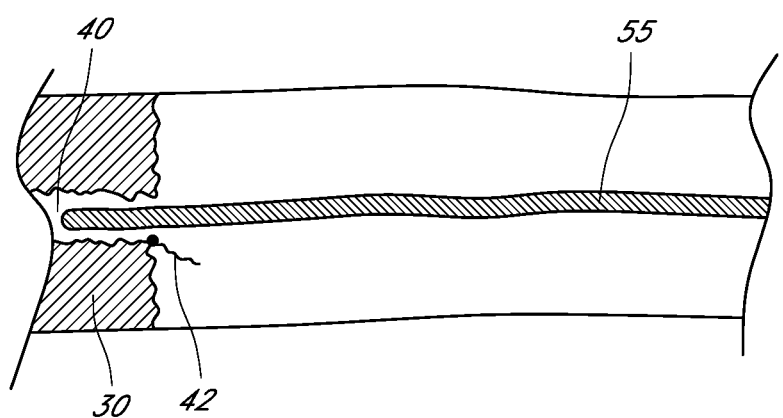

FIGS. 5A-5C schematically illustrate the mechanism of action of the inventive technology described herein that advantageously allows for facilitated traversal of occlusion (e.g., by a guidewire or contrast media). With reference to FIG. 5A, magnetic particles 15 (e.g., nanoparticles, microparticles) are introduced to the vessel 35 (e.g., systemically through intravenous or intra-arterial injection or via direct catheter injection adjacent to the occlusion 30. A rotating magnetic field 10 is applied to the magnetic particles 15 (e.g., by rotating a permanent magnet or manipulating currents within an electromagnet to create rotating magnetic fields) to create rotating stir bars 18 that generate micro-currents (as described in WIPO Publication No. WO 2011/053984 and WIPO Publ. No. WO 2013/173235 and in the description of FIGS. 6 and 7A-7C below). As schematically illustrated in FIG. 5B, the spinning action of the stir bars 18 and micro-currents acts to pry the hinged flap 42 open, thereby exposing the channel 40. The stir bars 18 can enter and highlight the channel 40, as described previously. As shown in FIG. 5C, with the flap 42 pried open, a guidewire or other instrument 55 and/or contrast media 20 can freely traverse the channel 40 without difficulty.

Figure 6A:
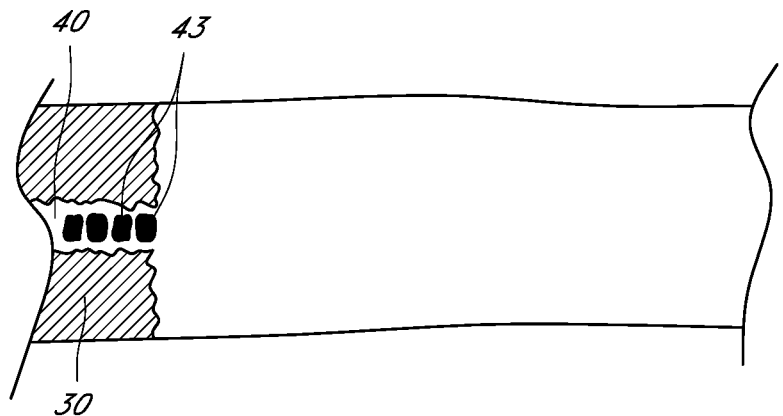
FIGS. 6A-6C schematically illustrate why cleaning out of debris from a channel of an occlusion or obstruction is difficult or impossible without use of the inventive technology described in the present application.
Figure 6B:
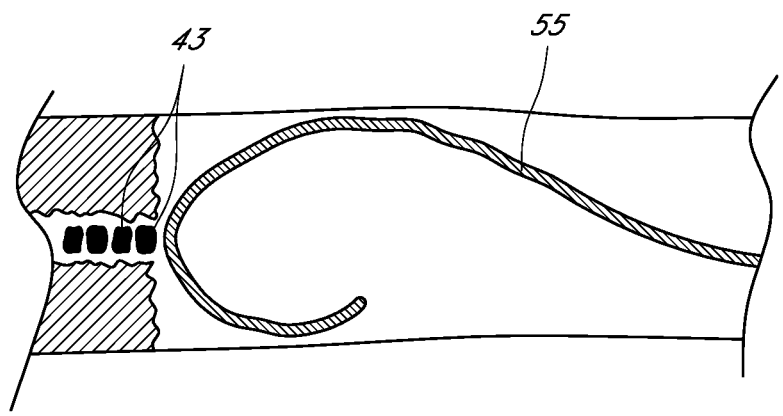
Figure 6C:
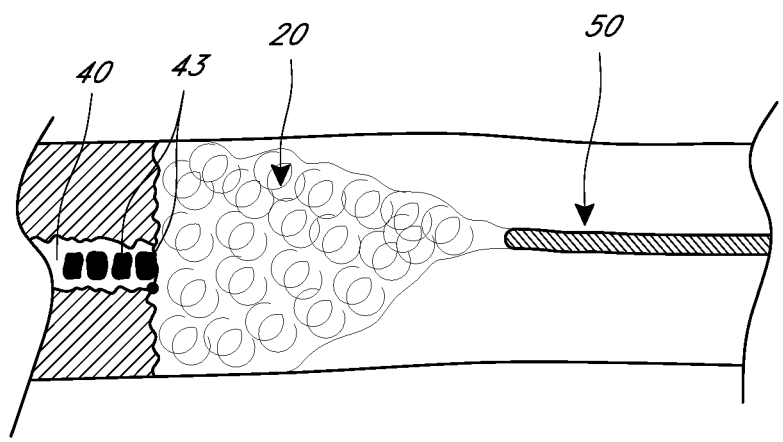

Turning to FIGS. 6A-6C, in some instances, debris 43 is present within the one or more channels 40 (e.g., microchannels) or voids 45 of a therapeutic target 30 (e.g., occlusion or obstruction), as shown in FIG. 6A. For example, an occlusion may include a larger channel that extends through a partial or entire length of the occlusion. The debris 43 may effectively block traversal of an occlusion 30 by a guidewire or other instrument 55, as shown in FIG. 6B. The debris 43 may compact when pushed on by the guidewire 55, thereby making it very difficult or impossible for the guidewire 55 to traverse the obstruction or occlusion 30 (similar to FIG. 4C). With reference to FIG. 6C, the debris 43 may also block (completely or partially) injected contrast media or agent 20 from entering or traversing the channel 40 of the occlusion 30 (similar to FIG. 4D). Thus, the debris effectively prevents the contrast media or agent 20 from being delivered within or beyond the occlusion 30.

Figure 7A:
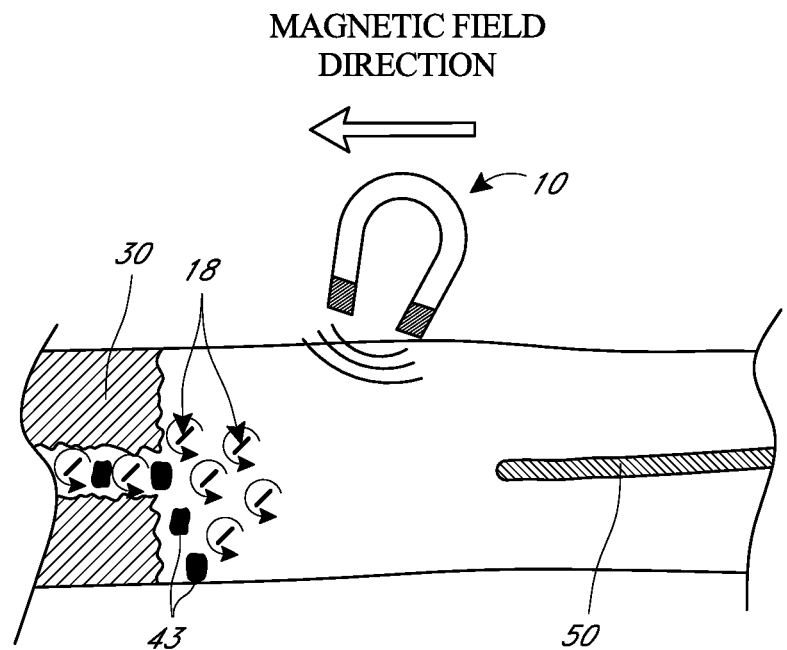
FIGS. 7A and 7B schematically illustrate the mechanism of action of the inventive technology described herein that advantageously allows for removal of debris from channels of an occlusion or obstruction.
Figure 7B:
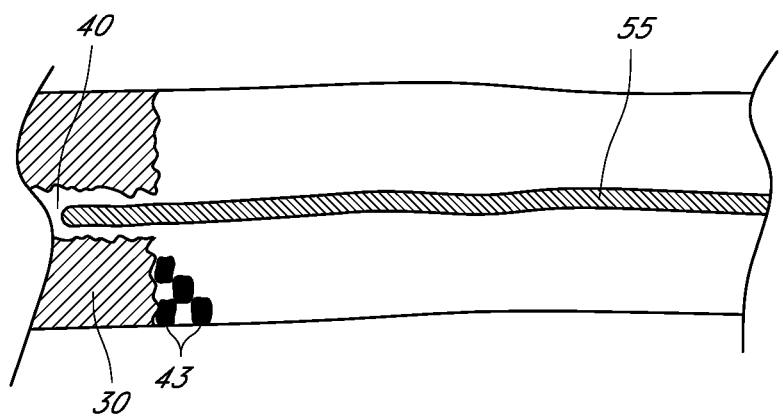

Similar to the mechanism illustrated in FIGS. 5A-5C, a rotating magnetic field can be applied by a magnetic control system 10 to the magnetic particles 15 (e.g., by rotating a permanent magnet or manipulating currents within an electromagnet to create rotating magnetic fields) to create rotating stir bars 18 that can move toward the occlusion 30 and within the channel 40 of the occlusion 30 even if the debris 43 is blocking or limiting flow through the vessel 35. The rotating stir bars 18 may also generate micro-currents as a result of the spinning action that cause the debris 43 to be "dug out" or removed from the channel 40, thereby unblocking the channel 40, as shown in FIG. 7A. With the debris 43 removed, a guidewire or other instrument 55 (and/or contrast media or agent 20, not shown) may now traverse the occlusion 30, as shown in FIG. 7B. In other words, the now open channel 40 allows for wire purchase, or access, through the occlusion 30. The open channel 40 also allows for contrast media or agent 20 to be delivered to locations downstream or beyond the occlusion 30.

Figure 8:
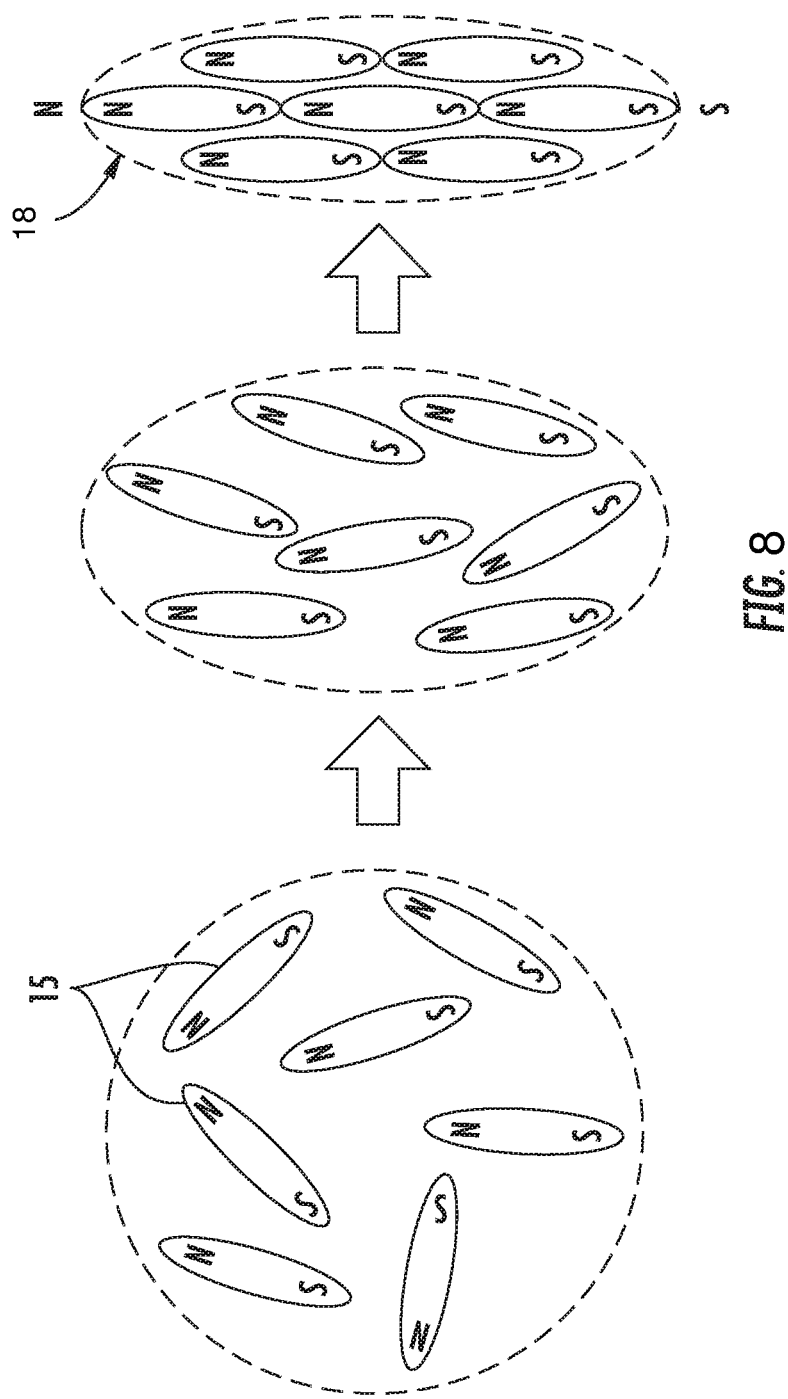
FIG. 8 schematically illustrates a sequence showing agglomeration of magnetic particles into an agglomerated structure under the influence of an applied magnetic field.

When a magnetic field is imposed on a collection of magnetic particles (e.g., nanoparticles), they can combine, or assemble, to form larger structures (e.g., agglomerates or agglomerated structures or ensembles or stir bars or stir rods). The size of these assembled structures can be related to an applied magnetic field strength, a size of the magnetic particles (e.g., nanoparticles), and/or a thickness of an optional coating on the magnetic particles (e.g., nanoparticles). FIG. 8 illustrates agglomeration of magnetic particles 15 into an assembled structure (e.g., a stir rod or stir bar or spheroid) 18 as a result of the applied magnetic field by the magnetic control system 10. The magnetic particles 15 can become magnetized and align due in part to the applied magnetic field. As the applied magnetic field increases in strength, the magnetic particles 15 can continue to become magnetized and align, assembling into a larger structure, such as the rod 18 depicted in FIG. 8. At a certain rotating magnetic field strength and field rotation frequency, depending on particle size and optional coating, the stir bars 18 will reach a saturation field and achieve a maximum length. In one embodiment, for uncoated magnetite particles, the particles are close to a saturation point when the applied magnetic field is approximately 0.2 T. In some embodiments, particle size can affect the strength and/or rigidity of the assembled structure. For example, when an assembled structure has an angular momentum, a likelihood that the assembled structure (e.g., stir bar) 18 will break apart is inversely related to the size of the magnetic nanoparticles 15 making up the assembled structure 18. Fully developed agglomerates 18 may contain a number of particles (e.g., nanoparticles), as many as ten or many more, depending on their size, and the magnitude of the rotating magnetic field. The agglomerates 18 are not stiff, depending on the magnetic field and gradient, and on the amount of magnetite in each particle 15 as well as the particle size.

In one example, a field of about 0.02 Tesla at the target site, in combination with a gradient of about 0.4 Tesla/meter, can create an agglomeration of magnetic particles (e.g., separated nanoparticle "stir rods" or "stir bars"). In general, the agglomerated structures (e.g., stir rods or stir bars) 18 can have a length that is greater than or equal to about 0.05 mm and/or less than or equal to about 3 mm in length, including but not limited to from about 0.05 mm to about 2 mm, from about 0.1 mm to about 2 mm, from about 0.2 mm to about 1.5 mm, from about 0.2 mm to about 1 mm, from about 0.3 mm to about 0.9 mm, from about 0.4 mm to about 0.8 mm, overlapping ranges thereof, less than 3 mm, less than 2 mm, less than 1.5 mm, less than 1 mm.

Figure 9A:
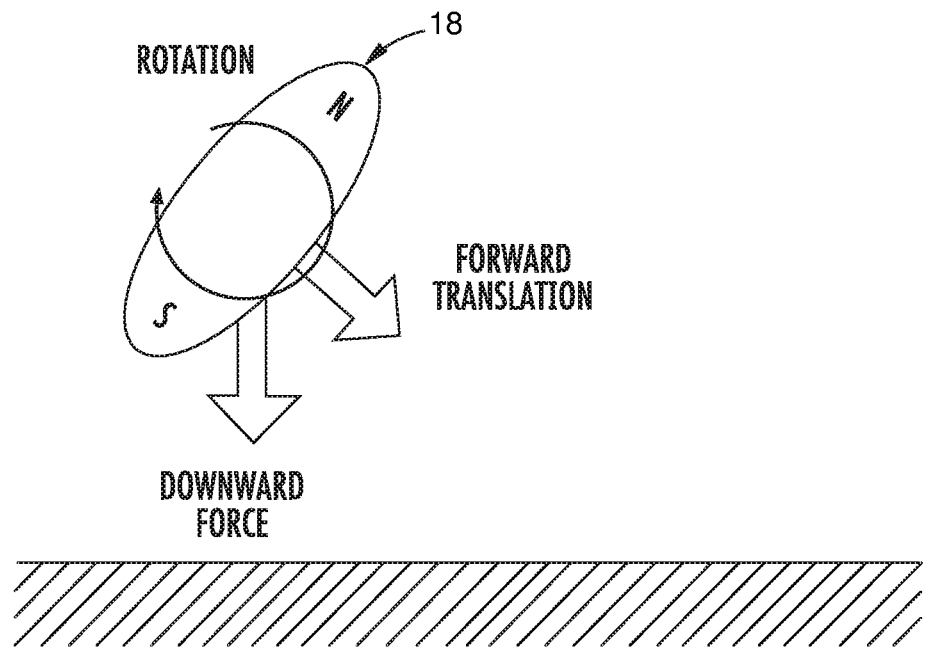
FIGS. 9A and 9B schematically illustrate an agglomerated structure rotating and translating as a result of a time-varying magnetic field and a gradient.

FIG. 9A illustrates an assembled structure 18, such as a stir rod or stir bar, rotating and translating as a result of a time-varying magnetic field applied by the magnetic control system 10. In some embodiments, the time-varying magnetic field 10 can rotate and can have a magnetic field gradient. This combination can result in a torque and a net force on the agglomerated structure. Due in part to the torque, the stir rod or stir bar 18 can rotate. The rotation and the net force can result in a forward translation of the agglomerated structure 18 as illustrated.

Figure 9B:
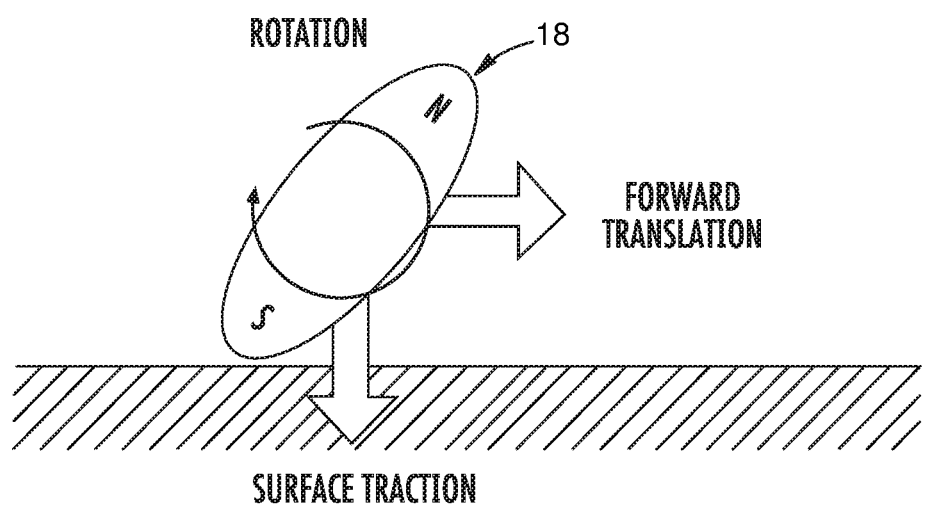

FIG. 9B illustrates an agglomerated structure 18 rotating and translating across a surface as a result of a time-varying magnetic field. If the agglomerated structure 18 comes into contact with a surface, a combination of the torque, force from the magnetic gradient, and friction between the agglomerated structure 18 and the surface can result in a forward translation. The motion of the agglomerated structure 18 can be end-over-end, similar to an ellipse or spheroid rolling along a surface.

As described with respect to FIGS. 9A and 9B, the agglomerated structure 18 can rotate and translate as a result of a time-varying magnetic field having a gradient. The stir rod or stir bar 18 can rotate and translate in a forward direction when in contact with a surface, to the right in FIG. 9B. Due in part to the rotation and translation of the agglomerated structures 18, a flow can be generated in a surrounding fluid, thereby generating micro-currents. As the agglomerated structure 18 moves (e.g., translates) forward it can experience a change in magnetic field. In some embodiments, the magnetic field can diminish with translation distance. As the gradient diminishes, the downward force on the agglomerated structure 18 can diminish. If the force diminishes past a threshold value, the agglomerated structure 18 can cease to be in contact with the surface, resulting in no friction force between the surface and the structure 18. The structure 18 can then experience a pressure arising from a flow of the fluid medium which surrounds the structure 18. This flow can result in a translation that is roughly backward, or left in FIG. 9B. As the structure 18 moves backward, the magnetic field gradient which the structure 18 experiences can increase and the structure 18 can be pulled back to the surface. Once back to the surface, the structure 18 can move forward in an end-over-end manner as explained above. The overall motion of the structure 18 can be generally circular or elliptical in nature. The end-over-end motion can facilitate travel of the structures 18 over complex terrains or surfaces within a patient's body.

Figure 9C:
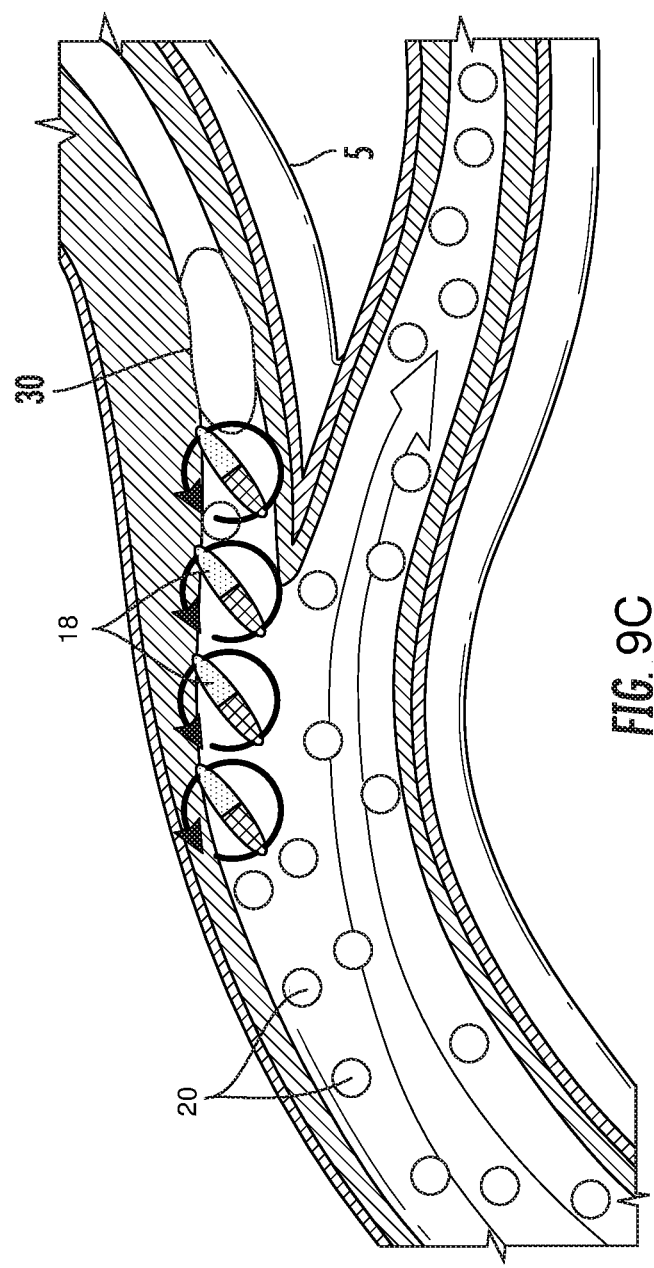
FIG. 9C schematically illustrates movement of multiple agglomerated structures toward a clot within a blood vessel.

With reference to FIG. 9C, in some embodiments, this flow pattern can increase mixing of a therapeutic and/or diagnostic agent (e.g., a thrombolytic, plasminogen, contrast agent, and/or theranostic agent or compound) or increase exposure of a therapeutic target 30 (e.g., a clot, a tumor) to a therapeutic agent. As shown in FIGS. 7A and 7B, the micro-currents may also facilitate removal of debris from within one or more channels 40 of an obstruction 30. In some aspects, the fluid can be a mixture of blood and a therapeutic agent (e.g., a thrombolytic drug), the blood and therapeutic agent being mixed by the generally circular motion of the agglomerated structures 20 to erode (e.g., lyse) and clear the therapeutic target 30. FIG. 9C illustrates how the movement of the agglomerated structures 18 can cause thrombolytic particles 20 to be "carried" or transported toward a fluid obstruction (e.g., clot) 30 even when there is little or no flow in a portion of a branch vessel 35 adjacent to the fluid obstruction 30.

By alternating a rotational direction of the magnetic stator system, the operator can direct the agglomerated structures (e.g., magnetic rotors) 18 within a vessel 35. For example, within a vessel, a velocity of blood increases with distance from the vessel wall, where the velocity is approximately zero. A clotted vessel branch will obstruct fluid flow resulting in the velocity dropping to zero at the opening of the branch. Within such low velocity regions, magnetic particles 15 generally assemble to be controlled by the magnetic stator system 10. When assembled, the magnetic stator system 10 can agglomerate the magnetic nanoparticles into larger structures 18 (e.g., magnetic rotors having an oblong shape). With a varying magnetic field, the magnetic rotors 18 can rotate, resulting in an end-over-end motion that results in the magnetic rotors traveling into or next to the blocked branches. The resulting rotational motion of the magnetic rotors can create new currents or increase low-velocity currents. The resulting currents can concentrate a therapeutic agent in an otherwise inaccessible or difficult to access region. By changing the rotation of the magnetic stator system 10, additional branches can be infused. For example, different rotational directions can result in the magnetic rotors 18 traveling to different branches. Rotational directions can be alternated to direct, or steer, magnetic rotors 18 to multiple branches. In accordance with several embodiments, the magnetic rotors need not contact the therapeutic target 30 to treat (e.g., reduce, erode, clear, or otherwise address) the target. For example, the magnetic rotors 18 can facilitate treatment (e.g., removal or erosion) of a thrombus or clot without scraping or contacting the clot or occlusion. In some embodiments, the magnetic rotors 18 infiltrate the target 30 (e.g., tumor) and deliver attached payload to the target 30.

FIG. 10 illustrates an example of a magnetic control system 10 in accordance with various implementations. The magnetic control system 10 can include a portable support base 102 and an arm positioner 112, as illustrated in FIG. 10. The system 10 can include a magnetic stator system configured to produce a desired magnetic field. For example, a magnetic stator system can include a neodymium-iron-boron permanent magnet block connected to a shaft and yoke assembly. In some embodiments, the yoke assembly is machined using carbon fiber plates to decrease weight and improve performance.

The permanent magnet block can be a single permanent magnet or multiple magnets. For example, the permanent magnet block can comprise two, three, four, six, eight, or some other number of NdBFe50 medium-temperature 2 inch cubes. A mechanical drive train can connect these assemblies to a pair of electric motors configured to vary in angulation and time to vary the magnetic field produced by the magnetic block. In some embodiments, the magnetic block can have a rotational frequency of at least about 1, 2 or 3 Hz and/or less than or equal to about 10 Hz (e.g., 2-4 Hz, 1-5 Hz, etc.) to produce a desired varying magnetic field. In some embodiments, the magnetic block is configured to produce a desired magnetic field at least about 6 inches from the surface of the magnetic block. In some embodiments, the magnetic block is configured to produce a magnetic field that is less than or equal to about 5 Gauss at about 54.6 cm inches from the magnetic block, and/or less than or equal to about 1 Gauss at about 94 cm from the block. In several embodiments, these mechanisms are housed in a protective cover that protects the operator and patient from mechanical hazards, as well as protects the elements and assemblies contained within the housing from hazards outside the housing.

The arm positioner 112 can be configured to position and/or orient the magnetic control system 10 in a desired location, such as adjacent to a patient's head, during treatment, or into a stowed position when not in use. The system 10 can include mechanisms to substantially secure the magnetic stator system in a desired location, such as locking or friction mechanisms. The system 10 can advantageously include a touchscreen interface module 100 configured to display information to the operator and receive input from the operator for use in controlling the system.

Positioning the magnet pod or block 110 of the magnetic control or stator system 10 can include using one or more mechanical features, e.g., the positioning assembly 112 (which may be composed of multiple independently controllable linkages or a single, unitary member) and portable support base 102, to position and/or orient the magnetic stator system 10 in a desired location relative to the patient. The positioning assembly 112 may include multiple pivots, joints, and/or hydraulic mechanisms that each can be adjusted individually or in combination. The positioning assembly 112 can adjust the magnet pod 110 along multiple axes or without restriction (e.g., six degrees of freedom) in order to provide precise positioning with respect to a patient. For example, the magnet pod 110 may be configured to rotate about two or more axes of rotation. The positioning assembly 112 may include locking mechanisms to prevent movement once a desired orientation and position is obtained. In some embodiments, the magnetic control system 10 can be positioned perpendicular to the patient's body (e.g., head, arm, or leg) at a distance of between 2 and 20 cm (e.g., between 2 and 6 cm, between 4 and 10 cm, between 6 and 12 cm, between 8 and 20 cm, overlapping ranges thereof, 8 cm, or any distance within the recited ranges) from the patient's body. The magnetic control system 10 can be configured to be substantially secured in place during use or it can be configured to move during use through manual operation, automatic operation, or some combination thereof.

In some embodiments, a rotating magnetic field is generated by mechanically rotating a strong permanent magnet having an orientation that rotates the field at a target site, and at the same time presents a steady magnetic gradient in a desired direction. Rotational frequencies (e.g., greater than or equal to 0.1 Hz and/or less than or equal to 100 Hz, including but not limited to from about 1 Hz to about 30 Hz, from about 3 Hz to about 10 Hz, from about 0.5 Hz to about 50 Hz, from about 1 Hz to about 6 Hz, from about 0.1 Hz to about 10 Hz, from about 5 Hz to about 20 Hz, from about 10 Hz to about 30 Hz, from about 20 Hz to about 50 Hz, from about 40 Hz to about 70 Hz, from about 50 Hz to about 100 Hz, overlapping ranges thereof, less than 5 Hz, less than 10 Hz, less than 20 Hz, less than 30 Hz, less than 40 Hz, less than 50 Hz) can be effective with a range of magnetic field magnitudes that can be generated by magnets (e.g., greater than or equal to 0.01 Tesla and/or less than 1 Tesla, including but not limited to from about 0.01 Tesla to about 0.1 Tesla, from about 0.05 Tesla to about 0.5 Tesla, from about 0.1 Tesla to about 0.6 Tesla, from about 0.3 Tesla to about 0.9 Tesla, from about 0.5 Tesla to about 1 Tesla, overlapping ranges thereof, less than 1 Tesla, less than 0.5 Tesla, less than 0.25 Tesla, less than 0.1 Tesla). Gradient strength can be greater than or equal to 0.01 Tesla/m and/or less than or equal to 10 Tesla/m, including but not limited to from about 0.01 Tesla/m to about 1 Tesla/m, from about 0.01 Tesla/m to about 3 Tesla/m, from about 0.05 Tesla/m to about 5 Tesla/m, from about 1 Tesla/m to about 4 Tesla/m, overlapping ranges thereof, less than 5 Tesla/m, less than 3 Tesla/m, less than 2 Tesla/m, less than 1 Tesla/m). The gradient direction generally centers on the center of mass for a permanent magnet.

In some embodiments, the systems comprise various features that are present as single features (as opposed to multiple features). For example, the systems may consist of a single permanent magnet as opposed to multiple magnets. In some embodiments, the systems comprise one or more of the following: means for controlling rotation of a magnet, means for delivering magnetic particles (e.g., intravenous or intra-arterial infusion assembly or intravascular catheter), etc.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. The headings used herein are merely provided to enhance readability and are not intended to limit the scope of the embodiments disclosed in a particular section to the features or elements disclosed in that section.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "advancing a catheter" include "instructing advancing a catheter." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 1000 nm" includes "1000 nm." Terms or phrases preceded by a term such as "substantially" or "generally" include the recited term or phrase. For example, "substantially continuously" includes "continuously."

What is claimed is:

1. A method of facilitating treatment of a therapeutic target within a body of a subject, the method comprising:
    delivering magnetic particles to a location near the therapeutic target within the body of the subject;
    applying a rotating magnetic field so as to cause the magnetic particles to agglomerate into stir bars and to generate a circulating motion adjacent the therapeutic target so as to cause at least some of the magnetic particles to be driven into an outer surface of the therapeutic target;
    obtaining images indicative of a shape of a profile or face outline of the outer surface of the therapeutic target using an imaging modality capable of imaging the magnetic particles;
    determining the shape of the profile or face outline of the outer surface of the therapeutic target based on the images; and
    selecting a particular instrument to penetrate or traverse through the therapeutic target based on the determined shape of the profile or face outline of the outer surface of the therapeutic target.

2. The method of claim 1, wherein applying the rotating magnetic field comprises rotating a permanent magnet positioned external to the subject.

3. The method of claim 2, wherein rotating the permanent magnet comprises rotating the permanent magnet at a frequency of between 1 Hz and 10 Hz, and wherein a magnitude of the magnetic field is between 0.01 and 1 Tesla.

4. The method of claim 1, wherein at least some of the magnetic particles comprise a diagnostic or theranostic agent.

5. The method of claim 1, further comprising delivering a therapeutic agent to the location of the therapeutic target.

6. The method of claim 1, further comprising delivering a diagnostic or theranostic agent to the location of the therapeutic target, wherein the circulating motion of the stir bars causes at least some of the diagnostic or theranostic agent to be driven into the outer surface of the therapeutic target, and wherein the imaging modality is configured to obtain images based on the diagnostic or theranostic agent.

7. The method of claim 1, wherein the imaging modality is selected from the group consisting of: a magnetic resonance imaging modality, an ultrasound-based imaging modality, and a tomography-based imaging modality.

8. The method of claim 1, wherein the determined shape of the profile or face outline of the outer surface of the therapeutic target is concave, convex or sloped and wherein the therapeutic target is a clot or a chronic total occlusion within a blood vessel.

9. The method of claim 1, wherein delivering the magnetic particles to the location near the therapeutic target within the body of the subject comprises injecting the magnetic particles locally through a catheter or using transdermal needle-guided access performed using the imaging modality.

10. The method of claim 1, wherein the magnetic particles and a diagnostic or theranostic agent are co-administered together at the same time.

11. The method of claim 1, wherein the magnetic particles and a diagnostic or theranostic agent are delivered separately.

12. A method of facilitating treatment of a therapeutic target within a body of a subject, the method comprising:
    delivering magnetic particles to a location near an occlusion within a blood vessel of the subject;
    applying a magnetic field so as to cause at least some of the magnetic particles to be driven into an outer surface of the occlusion;
    obtaining images indicative of a shape of a profile or face outline of the outer surface of the occlusion using an imaging modality capable of imaging the magnetic particles;
    determining the shape of the profile or face outline of the outer surface of the occlusion based on the images; and
    selecting an instrument to penetrate or traverse through the occlusion based on the determined shape of the profile or face outline of the outer surface of the occlusion.

13. The method of claim 12, wherein the occlusion is a clot or thrombus.

14. The method of claim 12, wherein the occlusion comprises a chronic total occlusion.

15. The method of claim 12, wherein the blood vessel is a peripheral artery, a cerebral artery, or a coronary artery.

16. The method of claim 12, wherein applying the magnetic field comprises rotating a permanent magnet positioned external to the subject.

17. The method of claim 16, wherein rotating the permanent magnet comprises rotating the permanent magnet at a frequency of between 1 Hz and 10 Hz, and wherein a magnitude of the magnetic field is between 0.01 and 1 Tesla.

18. The method of claim 12, wherein at least some of the magnetic particles comprise a diagnostic or theranostic agent.

19. The method of claim 12, wherein delivering the magnetic particles to the location near the occlusion within the blood vessel of the subject comprises injecting the magnetic particles locally through a catheter.

20. The method of claim 12, wherein delivering the magnetic particles to the location near the occlusion with the blood vessel of the subject comprises introducing the magnetic particles systemically through intravenous or intra-arterial injection.

* * * * *